(12) United States Patent
Takahashi

(10) Patent No.: US 11,690,501 B2
(45) Date of Patent: Jul. 4, 2023

(54) ILLUMINATION OPTICAL SYSTEM FOR ENDOSCOPE, OPTICAL ADAPTER FOR ENDOSCOPE, AND OPTICAL ELEMENT

(71) Applicant: Evident Corporation, Nagano (JP)

(72) Inventor: Susumu Takahashi, Iruma (JP)

(73) Assignee: Evident Corporation, Nagano (JP)

( * ) Notice: Subject to any disclaimer, the term of this patent is extended or adjusted under 35 U.S.C. 154(b) by 71 days.

(21) Appl. No.: 17/382,477

(22) Filed: Jul. 22, 2021

(65) Prior Publication Data
US 2022/0031145 A1 Feb. 3, 2022

(30) Foreign Application Priority Data

Aug. 3, 2020 (JP) .................................. 2020-131476
May 19, 2021 (JP) .................................. 2021-084567

(51) Int. Cl.
*A61B 1/002* (2006.01)
*A61B 1/06* (2006.01)
*A61B 1/00* (2006.01)

(52) U.S. Cl.
CPC .......... *A61B 1/002* (2013.01); *A61B 1/00096* (2013.01); *A61B 1/06* (2013.01)

(58) Field of Classification Search
CPC ............ A61B 1/00093; A61B 1/00163; A61B 1/00177; A61B 1/00179; A61B 1/002; A61B 1/0615; A61B 1/0623
See application file for complete search history.

(56) References Cited

U.S. PATENT DOCUMENTS

| 2012/0236380 | A1* | 9/2012 | Miyatake | B29D 11/00 359/204.1 |
| 2014/0071026 | A1* | 3/2014 | Hatash | G02B 5/0215 345/32 |
| 2019/0041627 | A1* | 2/2019 | Kobayashi | A61B 1/0615 |
| 2019/0107707 | A1* | 4/2019 | Takahashi | G02B 23/2423 |

FOREIGN PATENT DOCUMENTS

| JP | 2014-056050 A | 3/2014 |
| JP | 2015226712 A * | 12/2015 |
| JP | 6280818 B2 | 2/2018 |
| JP | 2019-069043 A | 5/2019 |

* cited by examiner

*Primary Examiner* — Aaron B Fairchild
*Assistant Examiner* — Julianna J Nicolaus
(74) *Attorney, Agent, or Firm* — Scully, Scott, Murphy & Presser, P.C.

(57) ABSTRACT

A light transmission optical member for endoscope includes an incident surface provided at a distal end portion of an insertion section, light being made incident on the incident surface as incident light from a proximal end side of the insertion section, and an emission surface for emitting the light as illumination light. The emission surface includes a diffusing section that diffuses the emitted light. The diffusing section includes a plurality of convex-shaped sections extending in a predetermined direction on the emission surface. Each of the convex-shaped sections includes a first slope section having a first angle with respect to the emission surface, and totally reflecting the incident light, and a second slope section having a second angle smaller than the first angle with respect to the emission surface, and transmitting and emitting reflected light totally reflected on the first slope section and the incident light.

14 Claims, 18 Drawing Sheets

ILLUMINATION OPTICAL SYSTEM FOR ENDOSCOPE, OPTICAL ADAPTER FOR ENDOSCOPE, AND OPTICAL ELEMENT

CROSS REFERENCE TO RELATED APPLICATION

This application claims benefit of Japanese Applications No. 2020-131476 filed in Japan on Aug. 3, 2020 and No. 2021-084567 filed in Japan on May 19, 2021, the entire contents of each of which are incorporated herein by their reference.

BACKGROUND OF THE INVENTION

1. Field of the Invention

The present invention relates to an illumination optical system for endoscope, an optical adapter for endoscope, and an optical element and, more particularly, to an illumination optical system for endoscope, an optical adapter for endoscope, and an optical element for diffusing emitted light.

2. Description of the Related Art

An endoscope is widely used in the industrial field and the medical field. The endoscope includes an insertion section and emits illumination light from a distal end of the insertion section. Reflected light of the illumination light reflected by an object is received by an observation window and an object image is acquired, whereby an object image in a subject is obtained.

As the endoscope, there are an endoscope for front view, an endoscope for side view, and the like. In order to uniformly irradiate an object with illumination light, a diffusing element including a diffusion surface for diffusing light is often provided in an illumination optical system.

For example, Japanese Patent Application Laid-Open Publication No. 2019-69043 proposes an illumination optical system for an endoscope in which an amount of light leaking to an outside without being totally reflected is reduced using a U-shaped prism to improve transmission efficiency of illumination light. In the endoscope according to the proposal, a diffusing element including a diffusion surface is provided in order to uniformly diffuse illumination light emitted from the U-shaped prism in all directions, that is, two-dimensional directions.

SUMMARY OF THE INVENTION

An illumination optical system for endoscope according to an aspect of the present invention is an illumination optical system for an endoscope including an insertion section configured to be inserted into a subject, the illumination optical system for endoscope including an optical element including an incident surface provided at a distal end portion of the insertion section, light being made incident on the incident surface as incident light from a proximal end side of the insertion section, and an emission surface for emitting the light as illumination light. The emission surface includes a diffusing section that diffuses the emitted light. The diffusing section includes a plurality of convex-shaped sections extending in a predetermined direction on the emission surface. Each of the convex-shaped sections includes a total reflection surface having a first angle with respect to the emission surface, the total reflection surface totally reflecting the incident light, and a transmission surface having a second angle smaller than the first angle with respect to the emission surface, the transmission surface transmitting and emitting reflected light totally reflected on the total reflection surface and the incident light.

An optical adapter for endoscope according to an aspect of the present invention is an optical adapter attachable to a distal end portion of an insertion section of an endoscope including the insertion section configured to be inserted into a subject, the optical adapter including: an optical element including an incident surface provided at the distal end portion, light being made incident on the incident surface as incident light from a proximal end side of the insertion section, and an emission surface for emitting the light as illumination light; and an illumination window for emitting the illumination light emitted from the emission surface of the optical element. The emission surface includes a diffusing section that diffuses the emitted light. The diffusing section includes a plurality of convex-shaped sections extending in a predetermined direction on the emission surface. Each of the convex-shaped sections includes a total reflection surface having a first angle with respect to the emission surface, the total reflection surface totally reflecting the incident light, and a transmission surface having a second angle smaller than the first angle with respect to the emission surface, the transmission surface transmitting and emitting reflected light totally reflected on the total reflection surface and the incident light.

An optical element according to an aspect of the present invention is an optical element including an incident surface on which light is made incident as incident light from a proximal end side and an emission surface for emitting the light as emitted light. The emission surface includes a diffusing section that diffuses the emitted light. The diffusing section includes a plurality of convex-shaped sections extending in a predetermined direction on the emission surface. Each of the convex-shaped sections includes a total reflection surface having a first angle with respect to the emission surface, the total reflection surface totally reflecting the incident light, and a transmission surface having a second angle smaller than the first angle with respect to the emission surface, the transmission surface transmitting and emitting reflected light totally reflected on the total reflection surface and the incident light.

DETAILED DESCRIPTION OF THE PREFERRED EMBODIMENTS

Embodiments of the present invention are explained below with reference to the drawings.

First Embodiment

Configuration of an Endoscope Apparatus

Figure 1:
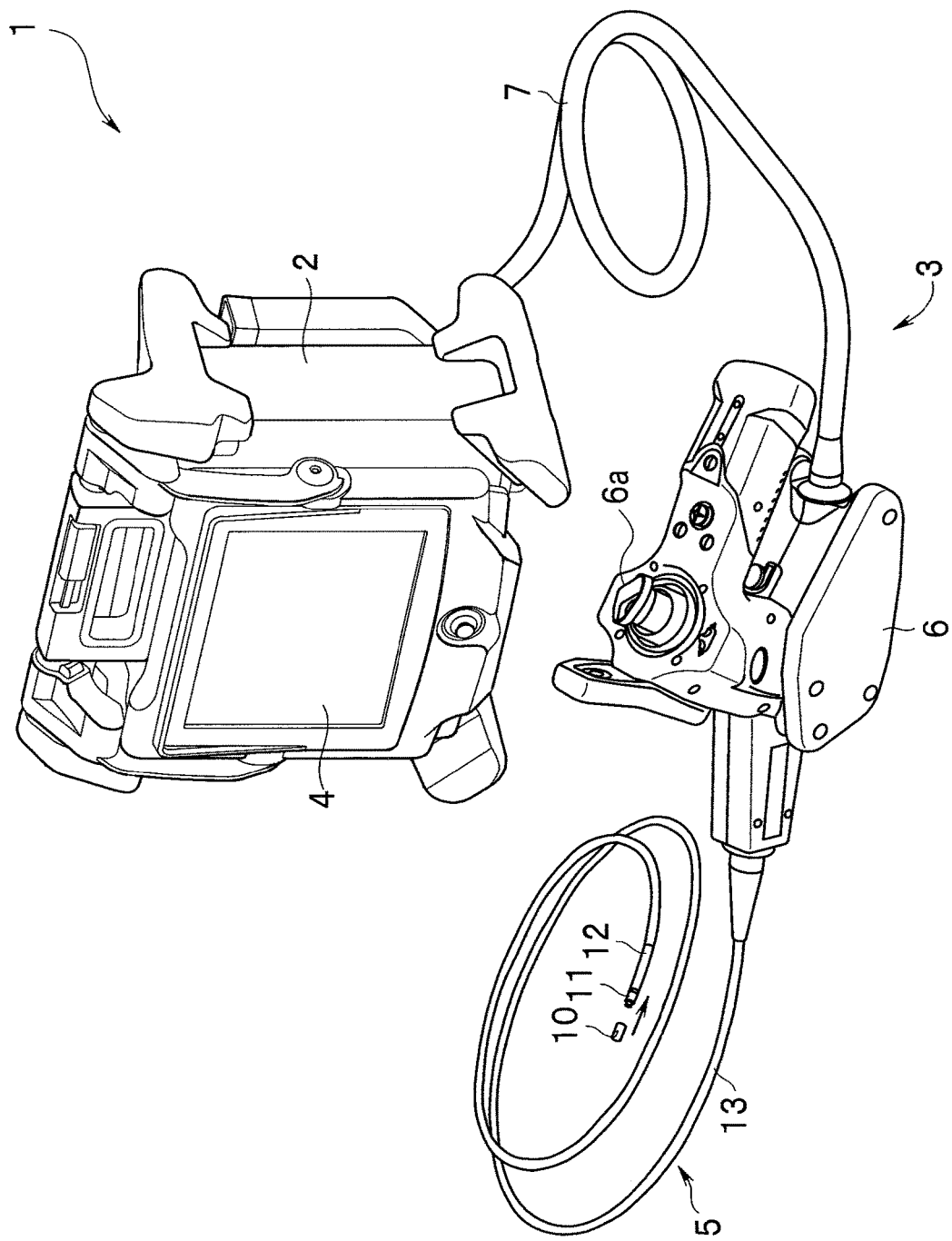
FIG. 1 is a configuration diagram showing a configuration of an endoscope apparatus according to a first embodiment of the present invention.

FIG. 1 is a configuration diagram showing a configuration of an endoscope apparatus according to a first embodiment.

As shown in FIG. 1, an endoscope apparatus 1 includes an apparatus main body 2 including a function of a video processor or the like and an endoscope 3 connected to the apparatus main body 2. The apparatus main body 2 includes a display unit 4 such as a liquid crystal display (LCD) on which an endoscopic image, an operation menu, and the like are displayed. A touch panel may be provided in the display unit 4.

The endoscope 3 includes an insertion section 5 functioning as an endoscope insertion section inserted into a subject, an operation section 6 consecutively connected to a proximal end of the insertion section 5, and a universal cord 7 extending from the operation section 6. The endoscope 3 is removably attachable to the apparatus main body 2 via the universal cord 7.

The insertion section 5 includes a distal end portion 11, a bending section 12, and a long flexible section 13 in order from a distal end side. The bending section 12 is consecutively connected to a proximal end of the distal end portion 11 and configured to be bendable in, for example, upward, downward, left, and right directions. The flexible section 13 is consecutively connected to a proximal end of the bending section 12 and has flexibility.

An image pickup device 11x (FIG. 4) such as a CMOS image sensor is incorporated in the distal end portion 11 of the insertion section 5. The image pickup device 11x receives incident light made incident on an observation window (not shown) provided at the distal end portion 11 of the insertion section 5.

As indicated by an arrow, an optical adapter 10 for side view is removably attachable to the distal end portion 11. By attaching the optical adapter 10 for side view to the distal end portion 11, the endoscope 3 is changed to an endoscope for side view. In other words, the optical adapter 10 is attachable to the distal end portion 11 of the insertion section 5 of the endoscope 3.

A bending joystick 6a for bending the bending section 12 in the upward, downward, left, and right directions is provided in the operation section 6. A user can bend the bending section 12 in a desired direction by tilting the bending joystick 6a. In the operation section 6, besides the bending joystick 6a, buttons for instructing endoscope functions, for example, various operation buttons such as a freeze button, a bending lock button, and a recording instruction button are provided.

Note that, in the case of a configuration in which the touch panel is provided in the display unit 4, the user may operate the touch panel to instruct various kinds of operation of the endoscope apparatus 1.

An endoscopic image picked up by the image pickup device 11x (FIG. 4) of an image pickup unit provided in the distal end portion 11 is displayed on the display unit 4 of the apparatus main body 2. Various circuits such as a control unit (not shown) that performs image processing and various kinds of control and a recording apparatus that records a processed image in a memory (not shown) are provided on an inside of the apparatus main body 2.

Configuration of the Optical Adapter

Figure 2:
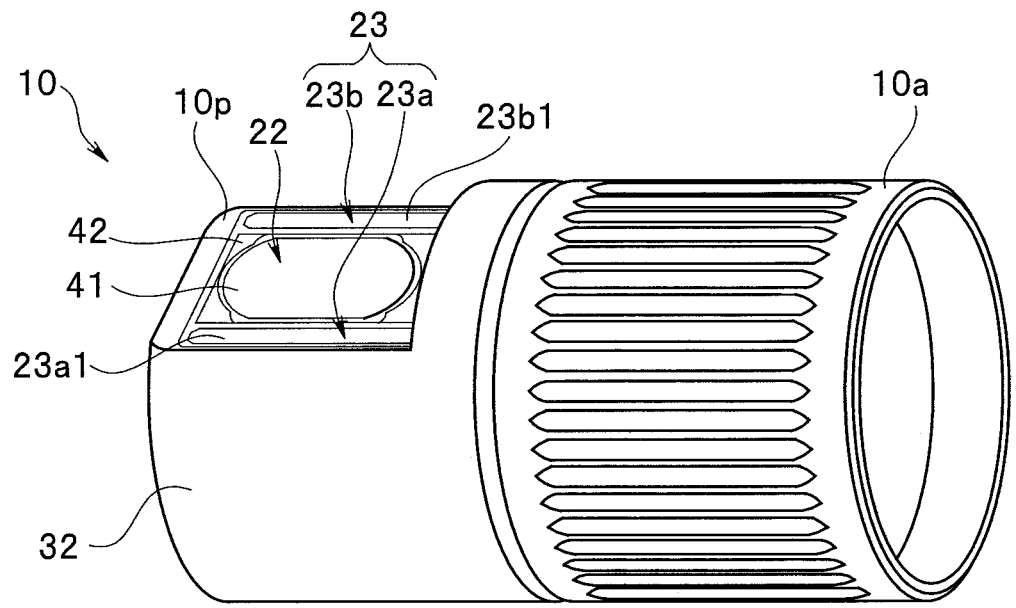
FIG. 2 is a perspective view of an optical adapter according to the first embodiment of the present invention.
Figure 3:
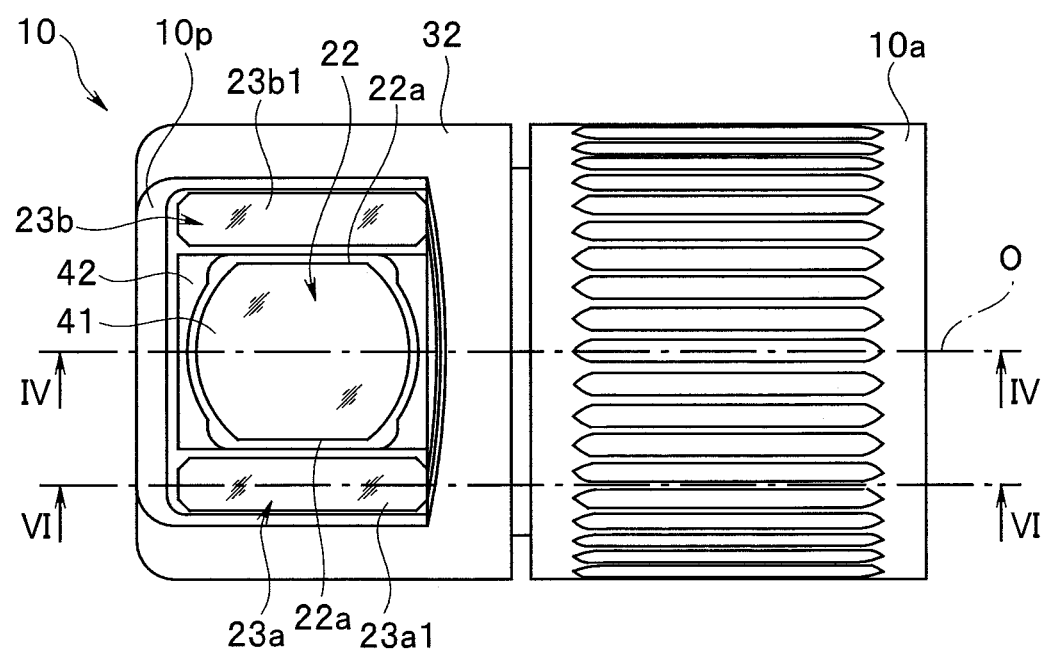
FIG. 3 is a plan view of the optical adapter viewed from a direction of a subject according to the first embodiment of the present invention.
Figure 4:
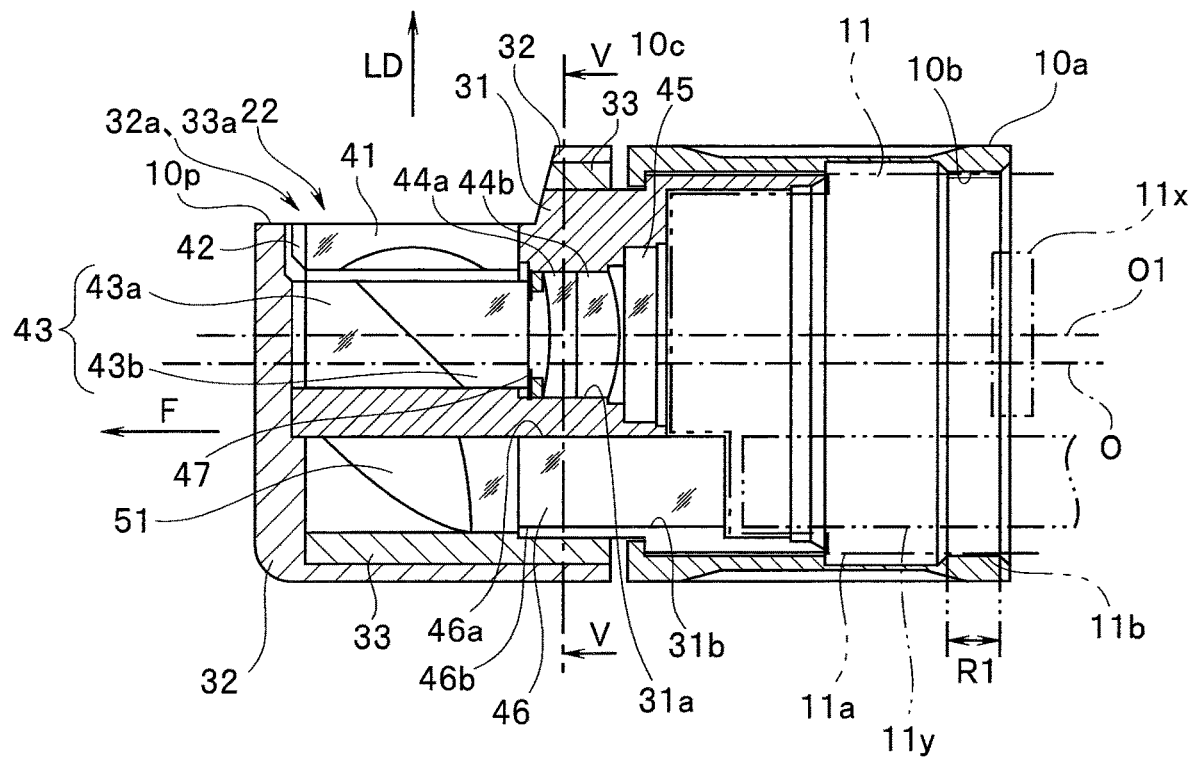
FIG. 4 is a sectional view of the optical adapter taken along a line IV-IV of FIG. 3.
Figure 5:
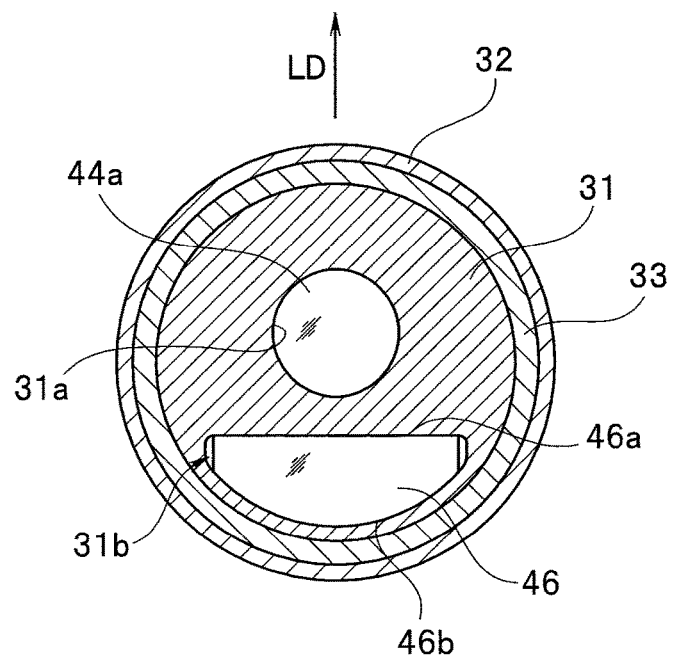
FIG. 5 is a sectional view of the optical adapter taken along a line V-V of FIG. 4.
Figure 6:
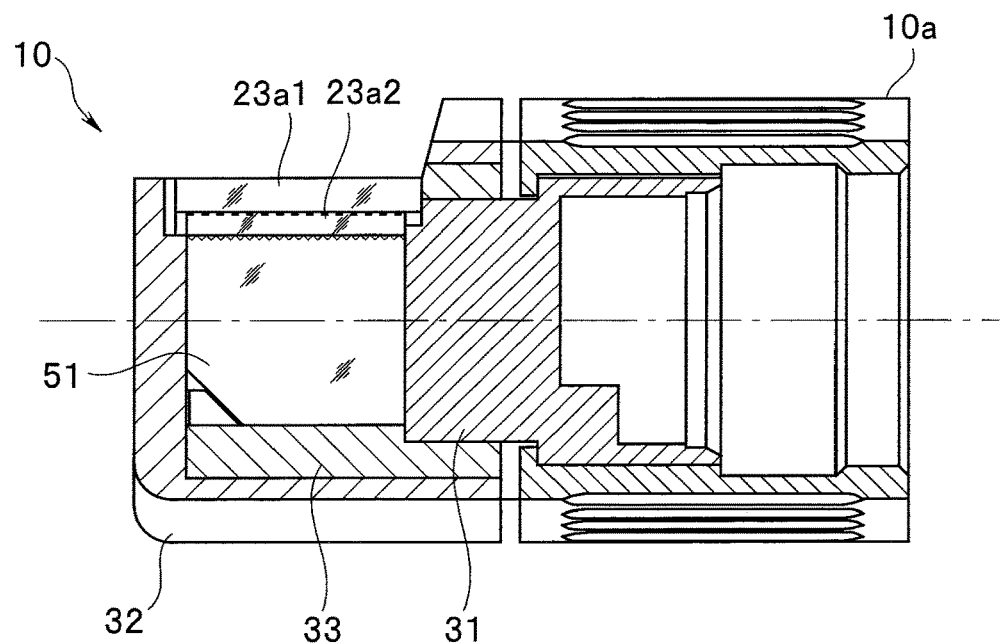
FIG. 6 is a sectional view of the optical adapter taken along a line VI-VI of FIG. 3.
Figure 7:
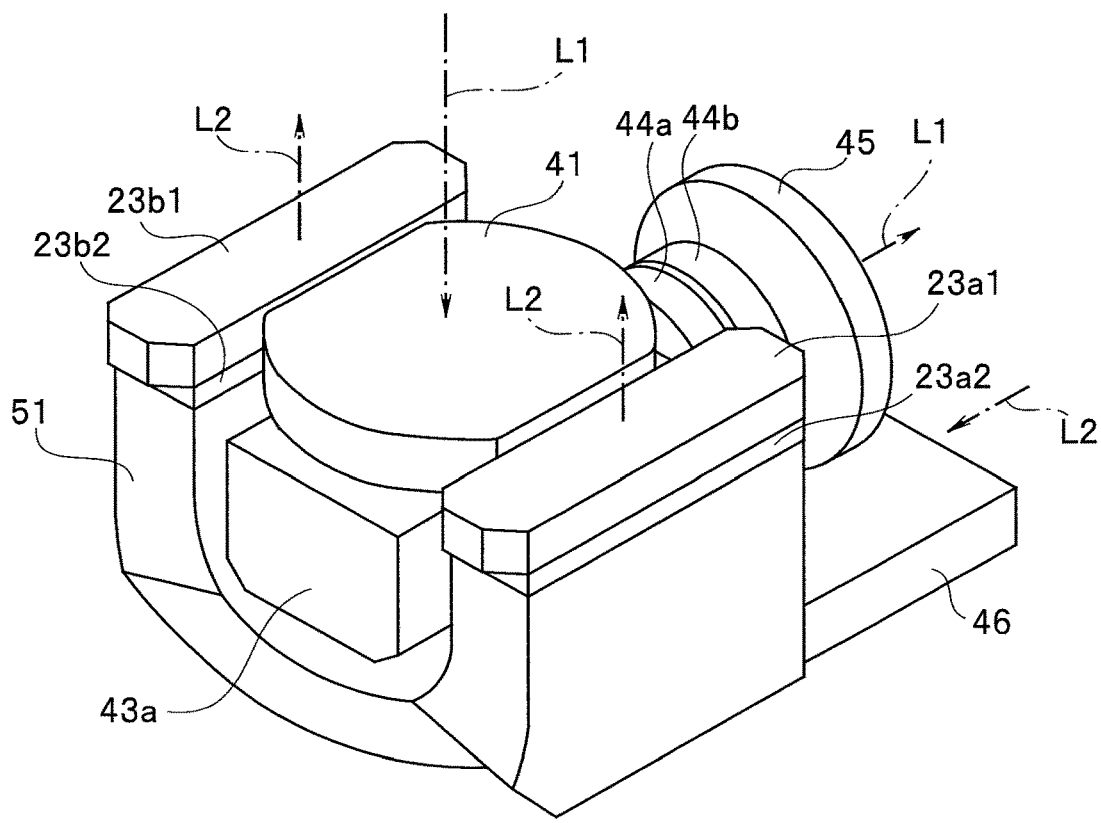
FIG. 7 is a perspective view of an image pickup optical system and an illumination optical system in the optical adapter according to the first embodiment of the present invention.
Figure 8:
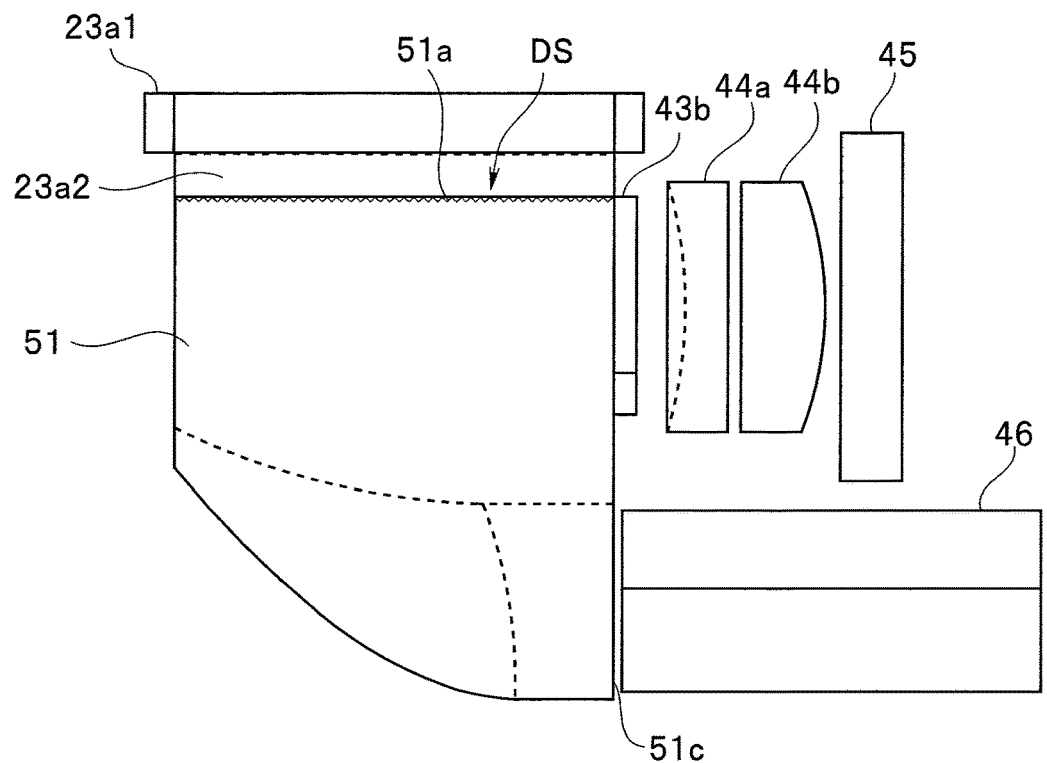
FIG. 8 is a front view of the image pickup optical system and the illumination optical system in the optical adapter according to the first embodiment of the present invention.
Figure 9:
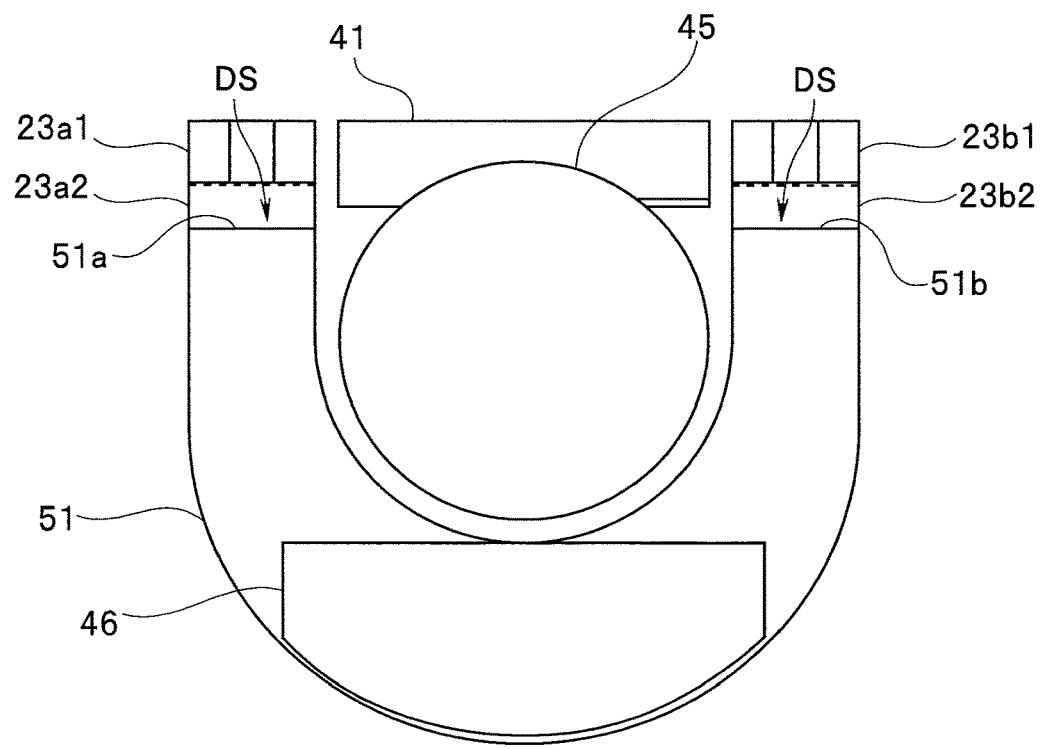
FIG. 9 is a right side view of the image pickup optical system and the illumination optical system in the optical adapter according to the first embodiment of the present invention.

FIG. 2 is a perspective view of the optical adapter 10. FIG. 3 is a plan view of the optical adapter 10 viewed from a direction of a subject. FIG. 4 is a sectional view of the optical adapter 10 taken along a line IV-IV of FIG. 3. FIG. 5 is a sectional view of the optical adapter 10 taken along a line V-V of FIG. 4. FIG. 6 is a sectional view of the optical adapter 10 taken along a line VI-VI of FIG. 3. FIG. 7 is a perspective view of an image pickup optical system and an illumination optical system in the optical adapter 10. FIG. 8 is a front view of the image pickup optical system and the illumination optical system in the optical adapter 10. FIG. 9 is a right side view of the image pickup optical system and the illumination optical system in the optical adapter 10.

As indicated by an alternate long and two short dashes line in FIG. 4, the distal end portion 11 of the insertion section 5 includes a distal end rigid member 11a having a cylindrical shape. A male screw section 11b is formed in a region R1 in a part of an outer circumferential surface of the distal end rigid member 11a.

The optical adapter 10 for side view has a columnar shape and includes a cylindrical stop ring 10a on a proximal end side. The stop ring 10a is capable of turning around a center axis (a center axis of the distal end portion 11) O (hereinafter referred to as axis O) of the insertion section 5. A female screw section 10b capable of screwing with the male screw section 11b is formed on an inner circumferential surface of a proximal end portion of the stop ring 10a. The axis O coincides with a center axis of the columnar optical adapter 10 when the optical adapter 10 is attached to the distal end portion 11.

The distal end rigid member 11a is inserted into an inner side of the stop ring 10a and the stop ring 10a is turned in a predetermined direction to screw the male screw section 11b and the female screw section 10b, whereby the optical adapter 10 can be attached and fixed to the distal end portion 11. When the stop ring 10a is turned in the predetermined direction, an inward flange section 10c provided at a distal end portion of the stop ring 10a presses a step section of an adapter main body 31 of the optical adapter 10. As a result, the optical adapter 10 is firmly fixed to the distal end portion 11.

By turning the stop ring 10a in an opposite direction of the predetermined direction, the optical adapter 10 can be detached from the distal end portion 11.

As shown in FIGS. 2 and 3, an observation window 22 for side view and two illumination windows 23a and 23b provided to sandwich the observation window 22 are disposed on a side surface on the distal end side of the optical adapter 10.

As shown in FIG. 3, in front view, the observation window 22 has a partial circular shape obtained by cutting both sides in the axis O direction to have two linear sections 22a. The two illumination windows 23a and 23b are disposed adjacent to the two linear sections 22a of the observation window 22. The observation window 22 takes in light from a side direction of the distal end portion 11 of the insertion section 5.

In front view, each of the illumination windows 23a and 23b has an elongated shape extending in parallel to the axis O and has, as shown in FIG. 3, a substantially quadrangle shape obtained by chamfering four corners of a rectangle.

As shown in FIG. 4, a cover member 32 is fixed to the adapter main body 31 to cover a distal end face of the adapter main body 31 of the optical adapter 10. The cover member 32 has a cylindrical shape closed on the distal end side. The columnar adapter main body 31 is disposed to fit in an inner side of a cylinder member 33. The cylinder member 33 is fixed to the adapter main body 31 by not-shown fixing means such as a screw. The cylinder member 33 is disposed to fit in an inner side of the cylindrical cover member 32. The cover member 32 is fixed to the cylinder member 33 by not-shown fixing means such as a screw.

The cover member 32 and the cylinder member 33 respectively include opening sections 32a and 33a formed by being cut in the axis O direction to pass positions separated by a predetermined distance in an outer diameter direction from the axis O. The observation window 22 and the two illumination windows 23a and 23b are disposed in the two opening sections 32a and 33a formed in the cover member 32 and the cylinder member 33.

In the observation window 22, a planoconcave lens 41 is positioned by a positioning section 42 and fixed to the adapter main body 31, the cover member 32, and the cylinder member 33 by an adhesive. A front surface of the planoconcave lens 41 is a flat surface. A rear surface of the planoconcave lens 41 is a concave surface. Note that the positioning section 42 is formed by a part of the adapter main body 31.

A prism unit 43 formed by two prisms 43a and 43b is disposed on a rear surface of the planoconcave lens 41.

A hole 31a having a cylindrical shape parallel to the axis O is formed in the adapter main body 31. A lens unit 44 formed by two lenses 44a and 44b disposed side by side along a center axis O1 of the hole 31a is disposed on a proximal end side of the prism unit 43 and is fixed in the hole 31a of the adapter main body 31 by an adhesive. A cover glass 45 is disposed on a proximal end side of the lens unit 44 and fixed in the hole 31a of the adapter main body 31 by an adhesive.

A bonding surface of the two prisms 43a, and 43b configures a reflection surface for reflecting light received from the planoconcave lens 41 toward the lens unit 44. The reflection surface can be configured by a metal film or a multilayer film. More specifically, the reflection surface can be formed of metal such as aluminum by coating. The reflection surface may be configured to simply direct totally reflected light toward the lens unit 44 without being subjected to treatment such as coating. Accordingly, the prism unit 43 is fixed to the adapter main body 31 by an adhesive to change a traveling direction of the light received from the planoconcave lens 41 by 90 degrees and emit the light toward the lens unit 44. The planoconcave lens 41, the prism unit 43, the lens unit 44, the cover glass 45, and a not-shown lens group in the distal end portion 11 configure an observation optical system of the endoscope 3. An optical axis of the prism unit 43 and the lens unit 44 does not coincide with the axis O.

As explained above, the planoconcave lens 41, the prism unit 43, the lens unit 44, and the cover glass 45 of the optical adapter 10 configure an observation optical system that emits light taken in from the observation window 22 from the distal end side toward the proximal end side along a longitudinal axis of the distal end portion 11. Note that a brightness aperture 47 is disposed on a proximal end portion side of the prism unit 43.

As shown in FIGS. 6 to 9, in the illumination window 23a, two optical members 23a1 and 23a2 stacked in a direction orthogonal to the axis O are positioned by the positioning section 42 and fixed to the adapter main body 31, the cover member 32, and the cylinder member 33 by an adhesive. The two optical members 23a1 and 23a2 are pasted together by an optical adhesive. As the optical adhesive, for example, a resin adhesive of a type hardened by being irradiated with an ultraviolet ray only has to be used.

In the illumination window 23b, as in the illumination window 23a, two optical members 23b1 and 23b2 stacked in the direction orthogonal to the axis O are positioned by the positioning section 42 and fixed to the adapter main body 31, the cover member 32, and the cylinder member 33 by an adhesive. The two optical members 23b1 and 23b2 are pasted together by an optical adhesive. The illumination windows 23a and 23b emit illumination light in a side direction of the distal end portion 11.

The optical members 23a1 and 23b1 are elongated tabular glass members. The optical members 23a2 and 23b2 respectively include diffusion surfaces (indicated by dotted lines in FIGS. 6, 8, and 9), which are sand grain surfaces machined into a frosted glass form, on surfaces on the optical members 23a1 and 23b1 sides. Light is diffused isotropically (at random) on the diffusion surfaces, which are the sand grain surfaces. Consequently, it is possible to further eliminate light distribution unevenness. The optical members 23a2 and 23b2 are respectively bonded to, on the diffusion surfaces of the optical members 23a2 and 23b2, the optical members 23a1 and 23b1 by an optical adhesive having a refractive index different from refractive indexes of the optical members 23a1 and 23b1 and the optical members 23a2 and 23b2. Light is scattered by the respective diffusion surfaces.

Note that, on contact surfaces with air of the sand grain surfaces of the glass members, since a refractive index difference is large and diffusibility is excessively large, light distribution excessively spreads. Therefore, in order to reduce a diffusion angle of sand grains to be a degree of spot erasing, the glass members are bonded by an optical adhesive having a refractive index of 1.52 or 1.56 (in the example, a refractive index of glass is 1.8).

Furthermore, when the sand grain surfaces explained above and a diffusion structure explained below are exposed to the air, the sand grain surfaces and the like are scratched or droplets adhere to the sand grain surfaces and the like and an optical characteristic changes when the endoscope 3 is used. Therefore, it is possible to prevent the scratches and the like by providing the optical members 23a1 and 23b1 as cover glasses.

Respective surfaces of the opening sections 32a and 33a of the cover member 32 and the cylinder member 33, the planoconcave lens 41, and the two optical members 23a1 and 23b1 are flat surfaces. Therefore, the optical adapter 10 includes a plane section 10p parallel to the axis O formed by these planes.

Illumination light is emitted in a direction LD (hereinafter referred to as illumination direction LD) orthogonal to the axis O from the illumination windows 23a and 23b.

In the adapter main body 31, a hole 31b for a rod lens 46 is formed in the axis O direction. A center of the hole 31b does not coincide with the axis O. The hole 31b is formed in the adapter main body 31 to deviate in an outer diameter direction from the axis O. The rod lens 46 is inserted through the hole 31b and fixed to the adapter main body 31 by an adhesive or the like. Accordingly, a sectional shape of the hole 31b substantially coincides with an outer diameter shape of the rod lens 46. As shown in FIG. 5, a sectional shape orthogonal to the axis O of the rod lens 46 is flat, a surface 46a on the axis O side of the rod lens 46 is a plane, and a surface 46b on the outer diameter direction side of the rod lens 46 has a partially cylindrical shape projecting in the outer diameter direction.

As shown in FIG. 4, a light guide 11y for illumination light is inserted through the insertion section 5. A distal end face of the light guide 11y is disposed to be opposed to a rear surface of an illumination window (not shown) of the distal end portion 11. The rod lens 46 is disposed in the optical adapter 10 such that the illumination window (not shown) of the distal end portion 11 is in a position opposed to a proximal end face of the rod lens 46 when the optical adapter 10 is attached to the distal end portion 11.

A light transmission optical member 51 is disposed on a distal end side of a distal end face of the rod lens 46 and is fixed to the adapter main body 31 by an adhesive or the like.

The illumination windows 23a and 23b, the light transmission optical member 51 and the rod lens 46 configure an illumination optical system for endoscope for the endoscope 3 including the insertion section 5 inserted into a subject.

As shown in FIG. 7, light L1 from the subject is made incident on the observation window 22 from a side direction of the optical adapter 10. The light L1 is made incident on the planoconcave lens 41, reflected by the prism unit 43, and emitted toward an image pickup optical system of the distal end portion 11 through the lens unit 44 and the cover glass 45.

Light L2 emitted from the distal end face of the light guide 11y of the distal end portion 11 is made incident on a proximal end face of the rod lens 46, made incident on an incident surface, which is a proximal end face, of the light transmission optical member 51 from the distal end face of the rod lens 46, emitted from an emission surface of the light transmission optical member 51, and emitted in the side direction of the optical adapter 10 from the two illumination windows 23a and 23b.

Configuration of the Light Transmission Optical Member 51

Subsequently, a configuration of the light transmission optical member 51 of the illumination optical system is explained.

Figure 10:
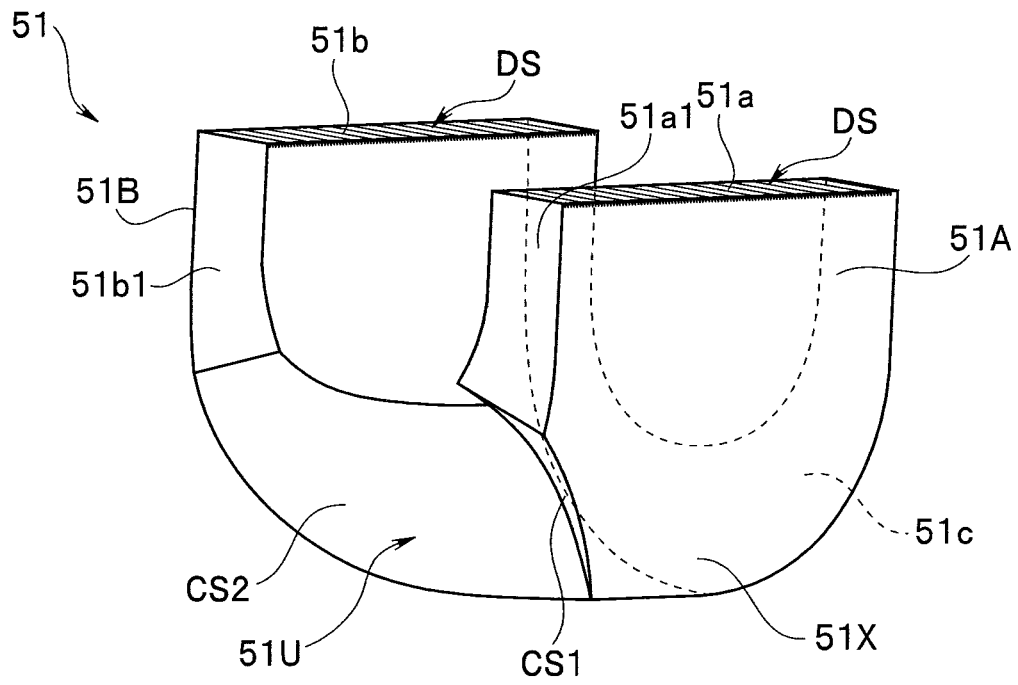
FIG. 10 is a perspective view of a light transmission optical member according to the first embodiment of the present invention.
Figure 11:
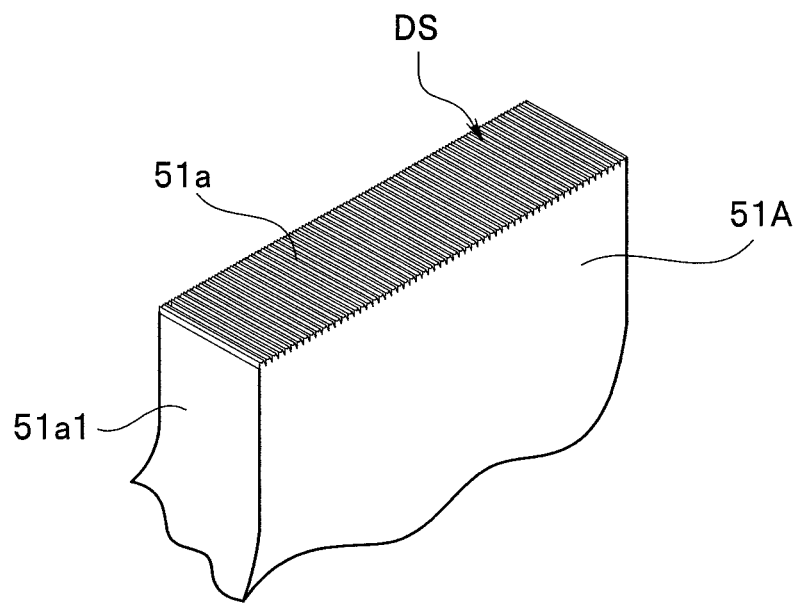
FIG. 11 is a perspective view of one of two extending sections of the light transmission optical member according to the first embodiment of the present invention.

FIG. 10 is a perspective view of the light transmission optical member 51. FIG. 11 is a perspective view of one of two extending sections of the light transmission optical member 51. A configuration and action of the light transmission optical member 51 in the present embodiment are substantially the same as a configuration disclosed in Japanese Patent Application Laid-Open Publication No. 2019-69043. Therefore, the configuration and the action of the light transmission optical member 51 are briefly explained here. Only components different from components disclosed in the publication are briefly explained.

As shown in FIG. 9, the light transmission optical member 51 is an optical member made of transparent glass or plastic having a substantial U shape when viewed in the axis O direction of the optical adapter 10.

The light transmission optical member 51 includes a partial cylinder section 51X and two extending sections 51A and 51B extending from both end portions in a circumferential direction of the partial cylinder section 51X. The prism unit 43 explained above is disposed in the substantially U-shaped light transmission optical member 51 to be surrounded by the partial cylinder section 51X and the two extending sections 51A and 51B.

In other words, the light transmission optical member 51 is a prism, a sectional shape of which viewed from a distal end side of a longitudinal axis is formed in a substantial U shape or a shape of a part of the substantial U shape such that an observation optical system is disposed on an inner side.

An emission surface 51a is formed on an end face of the extending section 51A. An emission surface 51b is formed on an end face of the extending section 51B. In the following explanation, in the light transmission optical member 51, a direction in which the emission surfaces 51a and 51b of the extending sections 51A and 51B are present is referred to as upper side direction as well.

Figure 12:
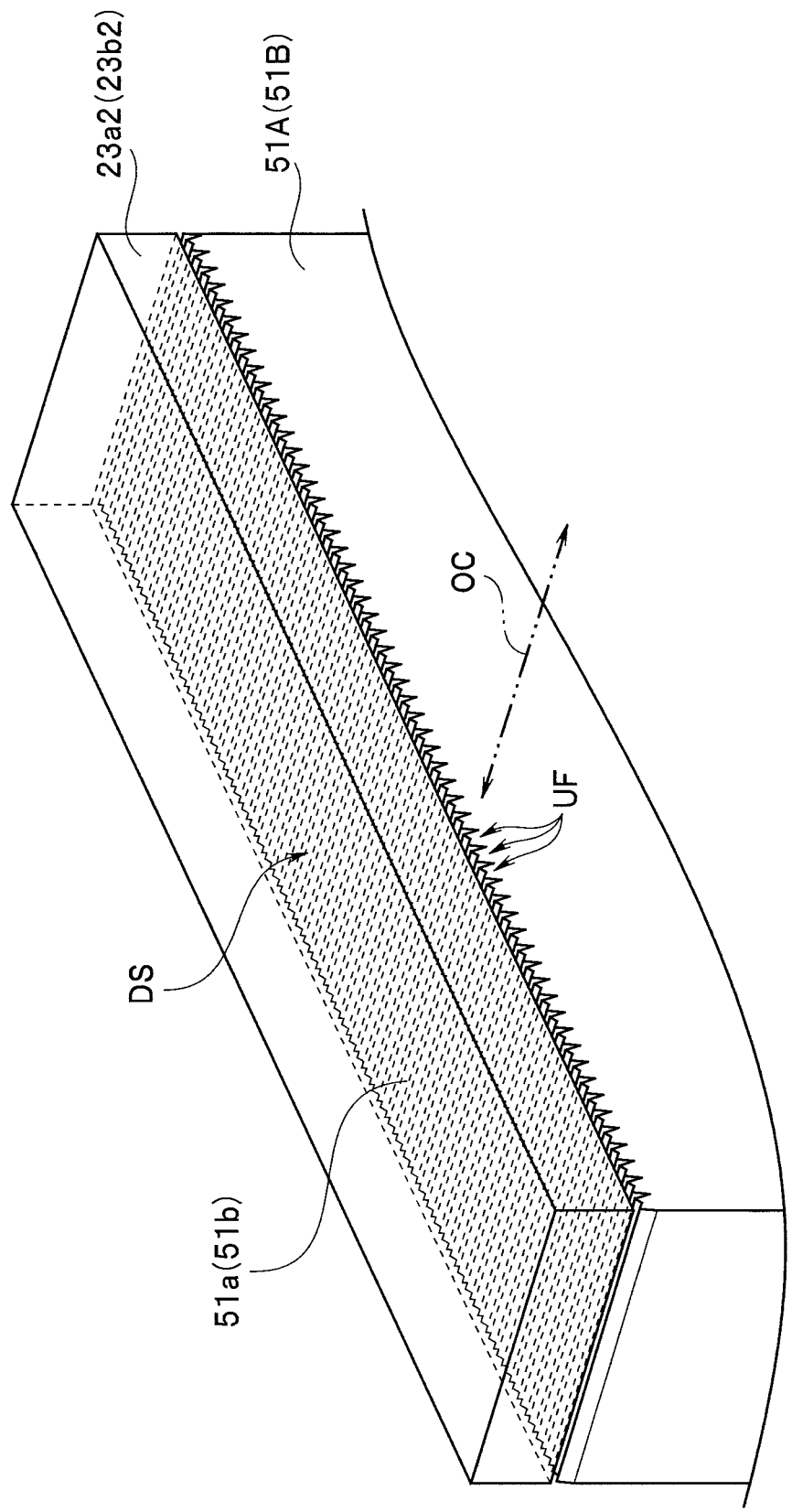
FIG. 12 is a perspective view of a diffusing section of each of the extending sections of the light transmission optical member and an optical member disposed on an upper side of a diffusion surface according to the first embodiment of the present invention.
Figure 13:
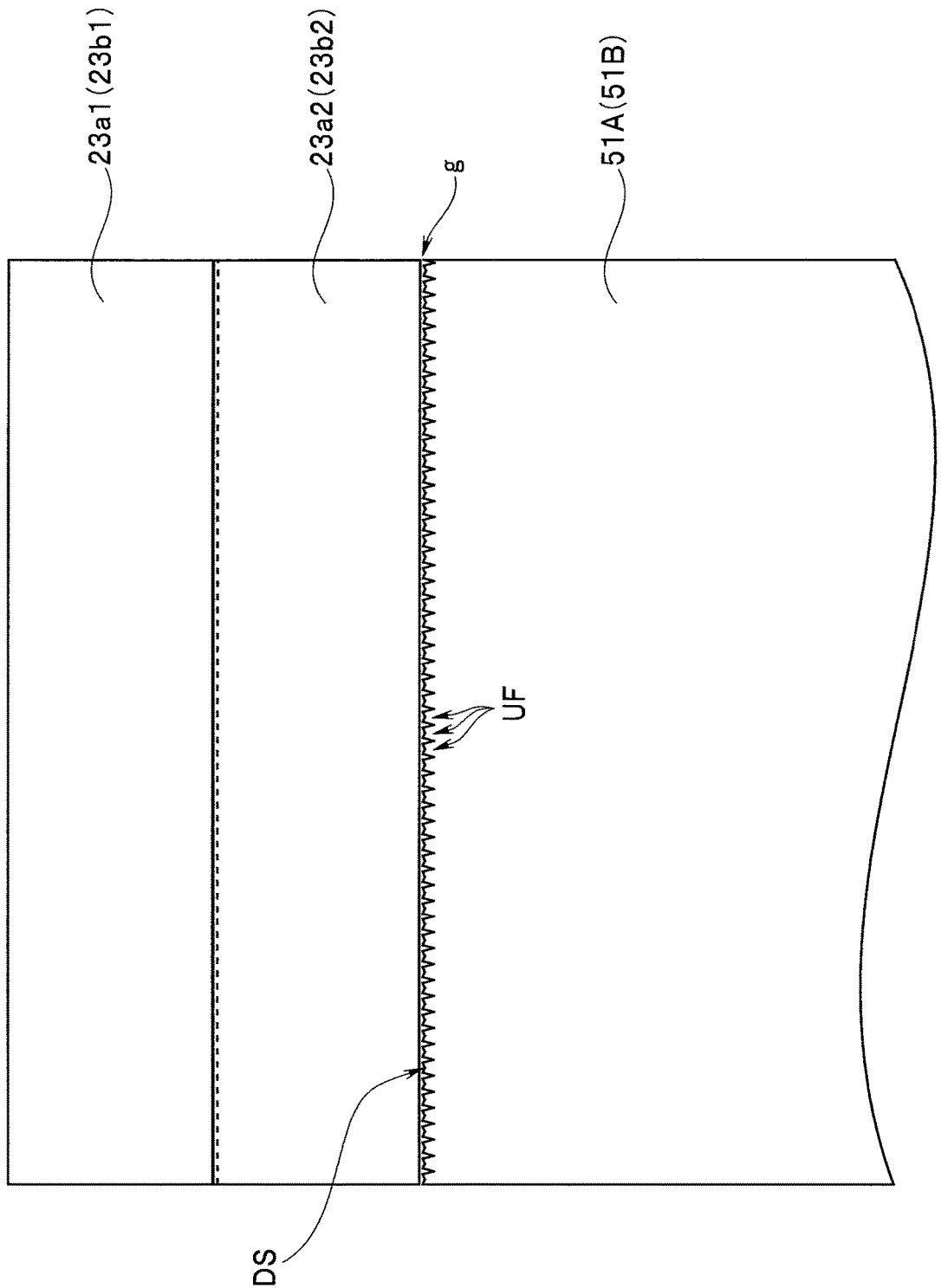
FIG. 13 is a side view of the diffusing section of each of the extending sections of the light transmission optical member and two optical members disposed on the upper side of the diffusion surface.

In the respective emission surfaces 51a and 51b, diffusing sections DS for diffusing light in a predetermined direction (in the present embodiment, a direction parallel to the axis O) are provided. The diffusing sections DS are formed using a molding technique. The diffusing sections DS include pluralities of convex-shaped sections UF (FIGS. 12 and 13). The pluralities of convex-shaped sections UF are formed to extend in the direction orthogonal to the axis O on the emission surfaces 51a and 51b. The diffusing sections DS are simultaneously formed when the light transmission optical member 51 is manufactured by molding using a mold. Accordingly, the diffusing sections DS can be formed by the molding when the light transmission optical member 51 is manufactured. Therefore, workability is high.

Note that the diffusing sections DS may be provided in the respective extending sections 51A and 51B by pasting tabular members including the diffusing sections DS to the respective emission surfaces 51a and 51b with an optical adhesive.

A plane section 51a1 is formed on a distal end side of the extending section 51A. A plane section 51b1 is formed on a distal end side of the extending section 51B. A plane section 51c having a substantial U shape is formed on a proximal end side of the light transmission optical member 51. A part of the plane section 51c, that is, a region opposed to the distal end face of the rod lens 46 is a light incident surface.

In other words, the light transmission optical member 51 is an illumination optical system and is provided at the distal end portion 11 of the insertion section 5. The light transmission optical member 51 is an optical element including the plane section 51c functioning as an incident surface and the emission surfaces 51a and 51b for emitting light as illumination light. The plane section 51c is an incident surface on which light is made incident on a proximal end side of the distal end portion 11 in a longitudinal axial direction of the insertion section 5. The emission surfaces 51a and 51b emit light as illumination light.

A concave section 51U is formed on a distal end side of the partial cylinder section 51X. The concave section 51U is formed in a substantial V shape when the light transmission optical member 51 is viewed from a subject on which illumination light is irradiated. Two reflection surfaces CS1 and CS2, which are curved surfaces, are formed in the concave section 51U of the light transmission optical member 51.

The two reflection surfaces CS1 and CS2 are provided plane symmetrically with respect to a plane passing the center axis of the distal end portion 11. The two reflection surfaces CS1 and CS2 are curved surfaces applied with reflection treatment such as aluminum coating. Note that a configuration may be adopted in which the reflection treatment such as coaling is not applied to the reflection surfaces CS1 and CS2 and the totally reflected light is simply directed to the emission surfaces 51a and 51b.

By providing the two reflection surfaces CS1 and CS2 in the concave section 51U, light reflected on the two reflection surfaces CS1 and CS2 can be made incident on an outer circumferential surface of the light transmission optical member 51 at an incident angle equal to or larger than a critical angle. Therefore, since almost all of light from the light guide is totally reflected and travels toward the two illumination windows. Consequently, it is possible to improve transmission efficiency of the light.

Configuration of the Diffusing Section DS

Figure 14:
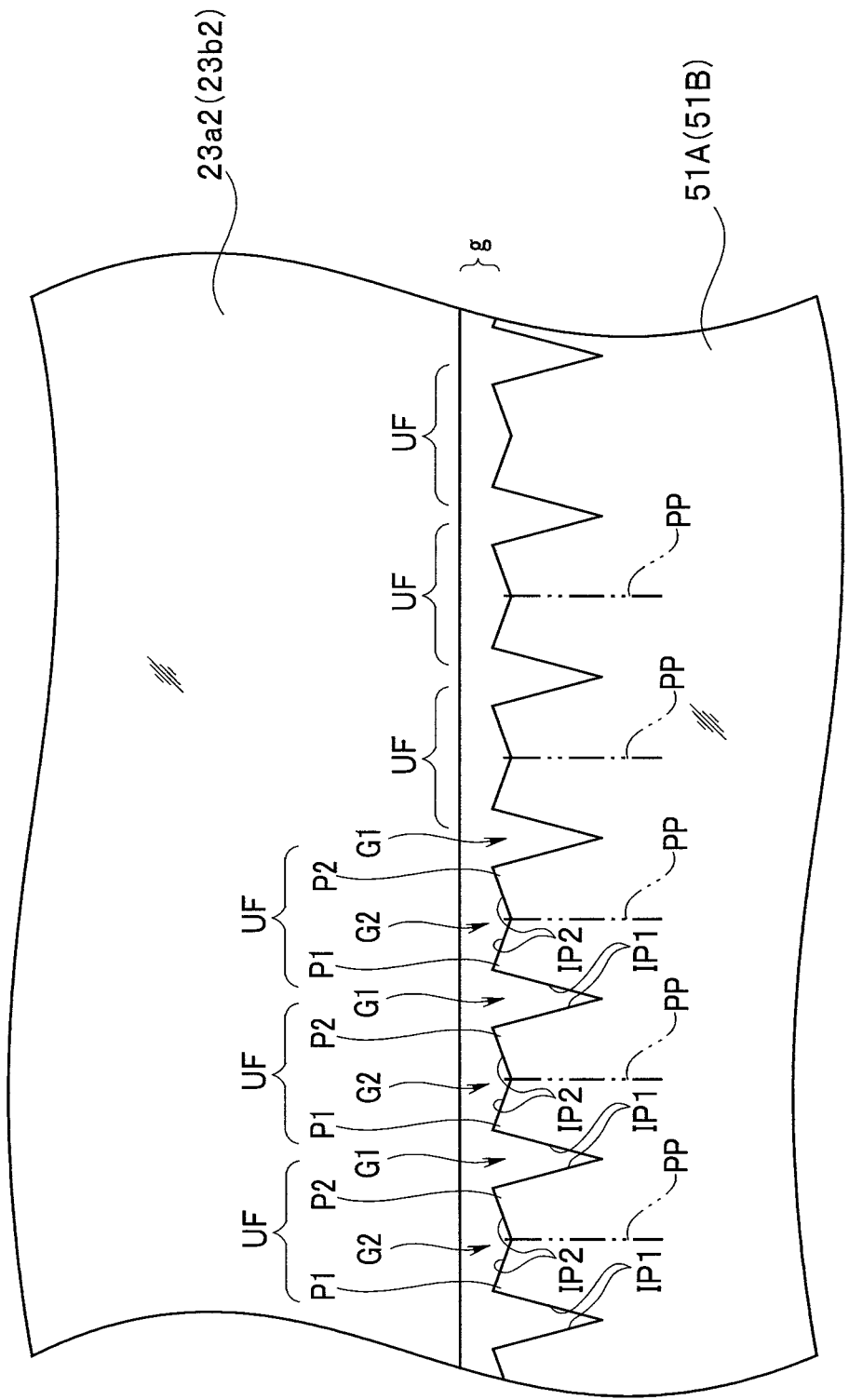
FIG. 14 is an enlarged side view of a part of the diffusing section of each of the extending sections of the light transmission optical member and the optical member disposed on the upper side of the diffusion surface according to the first embodiment of the present invention.

Subsequently, the diffusing section DS for light emitted from the substantially U-shaped light transmission optical member 51 is explained. FIG. 12 is a perspective view of the diffusing section DS of each of the extending sections of the light transmission optical member 51 and an optical member disposed on an upper side of the diffusion surface. FIG. 13 is a side view of the diffusing section DS of each of the extending sections of the light transmission optical member 51 and two optical members disposed on the upper side of the diffusion surface. FIG. 14 is an enlarged side view of a part of the diffusing section DS of each of the extending sections of the light transmission optical member 51 and the optical member disposed on the upper side of the diffusion surface.

The light transmission optical member 51 is made of plastic and has a refractive index of 1.5. The optical members 23a2 and 23b2 are disposed on the upper side of the emission surfaces 51a and 51b via a gap g of the air having a refractive index of 1. On the upper side of the optical members 23a2 and 23b2, the optical members 23a1 and 23b1 are respectively bonded and fixed by an optical adhesive (not shown). As shown in FIG. 13, the optical members 23a1 and 23b1 are bonded to the sand grain surfaces (indicated by a dotted lines) of the optical members 23a2 and 23b2 by an optical adhesive (not shown). The optical members 23a1, 23b1, 23a2, and 23b2 are made of glass and have a refractive index of 1.8.

Note that, on contact surfaces with air of the sand grain surfaces of the glass members, since a refractive index difference is large and diffusibility is excessively large, light distribution excessively spreads. Therefore, in order to reduce a diffusion angle of sand grains to be a degree of spot erasing, the glass members are bonded by an optical adhesive having a refractive index of 1.52 or 1.56 (in the example, a refractive index of glass is 1.8).

In the light transmission optical member 51 having the substantial U shape, light made incident on the plane section 51c is reflected on the two reflection surfaces CS1 and CS2. The light reflected on the two reflection surfaces CS1 and CS2, which are the curved surfaces, has a characteristic that the light widely diffuses in the direction orthogonal to the axis O and does not widely diffuse in the direction parallel to the axis O because of a reflection surface shape. Accordingly, in the direction parallel to the axis O, since the light does not diffuse, light distribution unevenness occurs. Even if the diffusing element that performs the isotropic light diffusion in the two-dimensional directions as in related art is used for the Light transmission optical member having such a light distribution characteristic, the light distribution unevenness is not improved. Besides, there is a problem that the light is diffused to an outside of a visual field as well by the diffusing element and a light amount in the visual field decreases.

Therefore, in the present embodiment, in order to diffuse the light in the direction parallel to the axis O, the diffusing sections DS formed by pluralities of convex-shaped sections UF formed in the direction orthogonal to the axis O direction are formed on the emission surfaces 51a and 51b of the respective extending sections 51A and 51B. The respective diffusing sections DS diffuse the light to the respective extending sections 51A and 51B in the axis O direction.

As shown in FIGS. 12 to 14, the diffusing section DS is formed to include the plurality of convex-shaped sections UF formed on the emission surface 51a or 51b of each of the extending sections 51A and 51B. More specifically, the diffusing section DS includes the plurality of convex-shaped sections UF linearly extending in a predetermined direction on the emission surface 51a or 51b. In other words, each of the convex-shaped sections UF is formed to linearly extend in a direction OC orthogonal to the axis O on the emission surface 51a or 51b. As shown in FIG. 14, each of the convex-shaped sections UF has two slope sections IP1 and two slope sections IP2. Each of the convex-shaped sections UF includes two convex sections P1 and P2. As shown in FIG. 14, the slope sections IP1 are steep slopes and the slope sections IP2 are gentle slopes having an inclination angle smaller than an inclination angle of the slope sections IP1.

The two convex sections P1 and P2 of each of the convex-shaped sections UF are also formed to linearly extend in the direction OC. The convex section P1 is formed by one of the two slope sections IP1 and one of the two slope sections IP2. The convex section P2 is formed by the other of the two slope sections IP1 and the other of the two slope sections IP2.

A groove G1 is formed by the two slope sections IP1 between the two convex-shaped sections UF adjacent to each other. A groove G2 is formed by the two slope sections IP2 plane symmetrical with respect to a plane PP of each of the convex-shaped sections UF. A plurality of grooves G1 and G2 are disposed in parallel and alternately one another.

Figure 15:
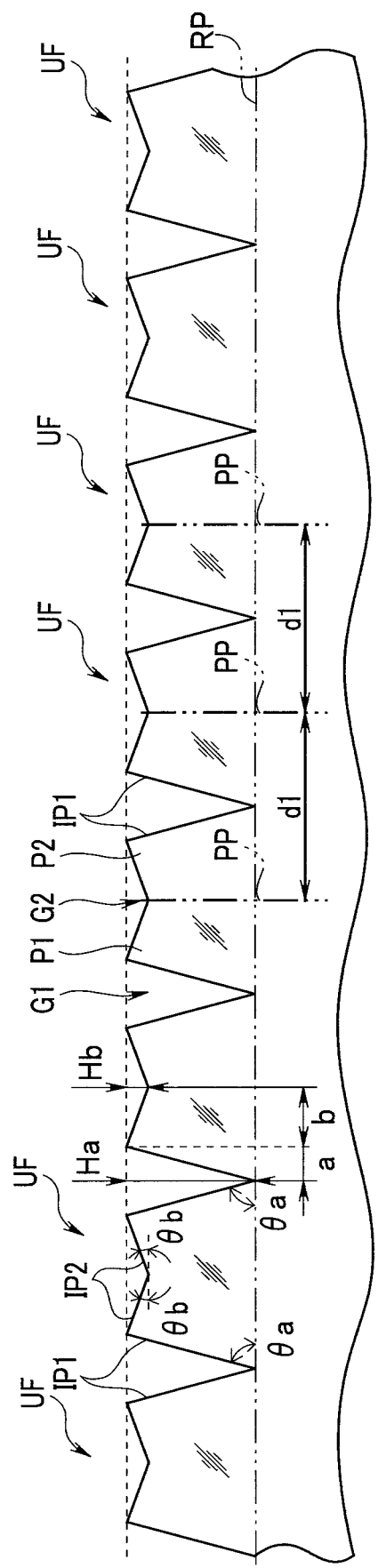
FIG. 15 is a sectional view showing a shape of cross sections of a plurality of convex-shaped sections according to the first embodiment of the present invention.

FIG. 15 is a sectional view showing a shape of cross sections of the plurality of convex-shaped sections UF. FIG. 15 shows a cross section of a part of the diffusing section DS at the time when the emission surface 51a or 51b is viewed from the direction OC. As shown in FIG. 15, the slope sections IP1 and IP2 of each of the convex sections P1 respectively have angles θa and θb with respect to an imaginary plane (that is, a surface parallel to the emission surface 51a or 51b) RP parallel to the direction OC. The angle θb is smaller than the angle θa.

As explained above, the convex section P2 has the shape plane symmetrical to the convex section P1 with respect to the plane PP. Accordingly, the slope sections IP1 and IP2 of each of the convex sections P2 also respectively have the angles θa and θb with respect to an imaginary plane RP parallel to the direction OC.

Figure 16:
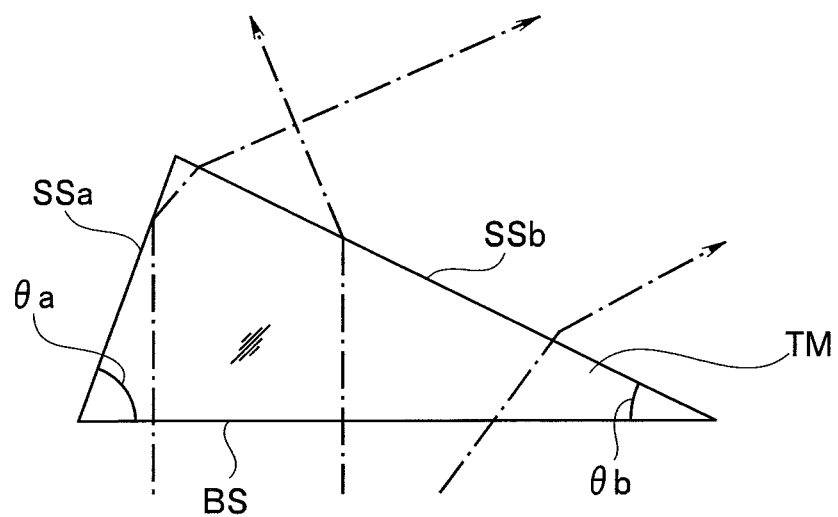
FIG. 16 is a sectional view of a triangular prism member in minimum unit defining a shape of two slope sections of each of the convex-shaped sections according to the first embodiment of the present invention.
Figure 17:
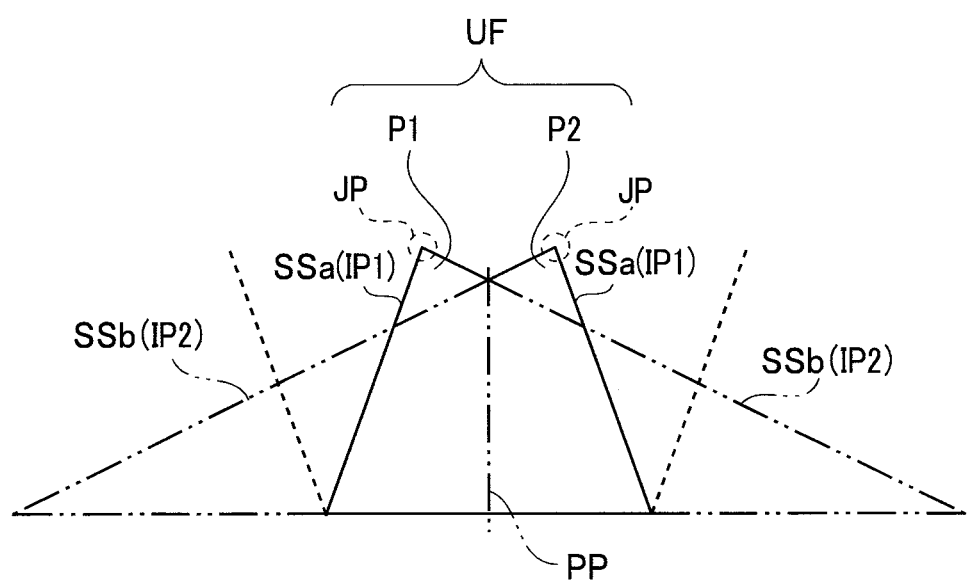
FIG. 17 is a diagram for explaining a sectional shape of each of the convex-shaped sections according to the first embodiment of the present invention.

A shape of the convex-shaped section UF is explained in detail. FIG. 16 is a sectional view of a triangular prism member TM in minimum unit MU defining a shape of the two slope sections IP1 and IP2 of each of the convex-shaped sections UF. FIG. 17 is a diagram for explaining a sectional shape of each of the convex-shaped sections UF.

The minimum unit MU has a shape of a triangular prism member TM, a cross section of which has a triangular shape shown in FIG. 16. A shape of the plurality of convex sections P1 and P2 is defined based on the shape of the minimum unit MU. As shown in FIG. 16, the triangular prism member TM, the sectional shape of which is the triangular shape, includes a bottom surface section BS, a slope section SSa having an angle (an interior angle) θa with respect to the bottom surface section BS, and a slope section SSb having an angle (an interior angle) θb with respect to the bottom surface section BS. The shape of each of the convex-shaped sections UF is defined based on a shape of the two slope sections SSa and SSb.

As shown in FIG. 17, a shape of the two convex sections P1 and P2 is defined based on two slope sections SSa and two slope sections SSb at a time when the triangular prism member TM is formed plane symmetrical with respect to the plane PP passing one point on the slope section SSb, parallel to an axis of the triangular prism member TM, and orthogonal to the bottom surface section BS. The slope sections IP1 and 1P2 forming each of the convex sections P1 and P2 respectively correspond to parts of the two slope sections SSa and SSb of the triangular prism member TM.

As shown in FIG. 12, the diffusing section DS is an uneven section formed by being disposed on the emission surface 51a or 51b. The uneven section is formed by disposing the plurality of convex-shaped sections LIF at a predetermined interval d1 in the axial direction parallel to the axis O. Each of the convex-shaped sections OF includes the two convex sections P1 and P2. The convex section P1 or P2 is formed by the two slope sections IP1 and IP2. In other words, the diffusing section DS has a shape formed by the plurality of convex-shaped sections UF disposed in the axial direction parallel to the axis O on the emission surface 51a or 51b of each of the extending sections 51A and 51B.

Note that a bonded section JP of the slope sections IP1 and IP2 in each of the convex sections P1 and P2 may not be sharp and, for example, may have a round shape or may have a chamfered shape cut on multiple surfaces.

Diffusion and Light Distribution of Illumination Light

Subsequently, diffusion and light distribution of illumination light are explained.

As shown in FIG. 15, each of the convex-shaped sections UF includes the two slope sections IP1 and IP2 plane symmetrical with respect to the plane PP orthogonal to the axis O. The convex section P1 of each of the convex-shaped section UF has a shape plane symmetrical to the convex section P2 with respect to the plane PP. Since each of the convex-shaped sections OF have the shape plane symmetrical with respect to the plane PP, light distribution unevenness is prevented from occurring in the left-right direction.

Figure 18:
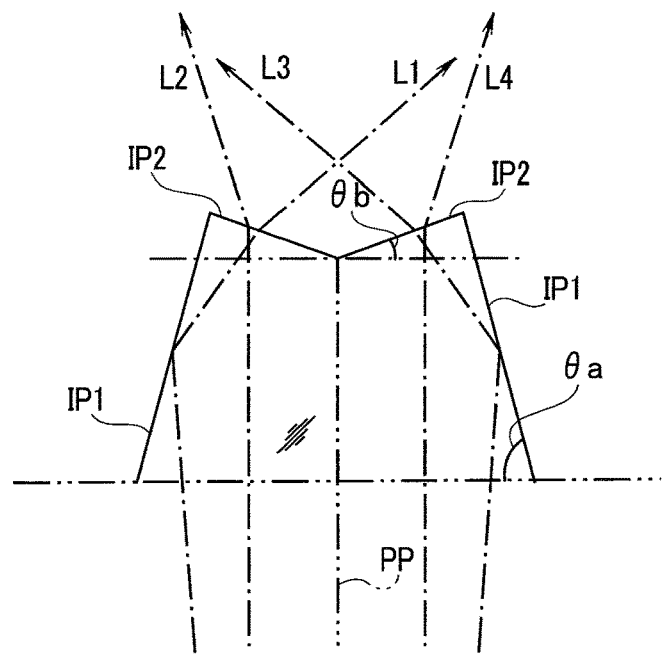
FIG. 18 is a diagram for explaining an optical path in the diffusing section according to the first embodiment of the present invention.

FIG. 18 is a diagram for explaining an optical path in the diffusing section DS. Light travels toward the diffusing section DS and is made incident to spread by approximately 60°. As shown in FIG. 18, a part of the light traveling toward the diffusing section DS is totally reflected on the slope section IP1 of the convex section P1 and refracted on the slope section IP2 to be light L1 to be emitted. Another part of the light traveling toward the diffusing section DS is made incident on the slope section IP2 of the convex section P1 and refracted on the slope section IP2 to be light L2 to be emitted.

Figure 27:
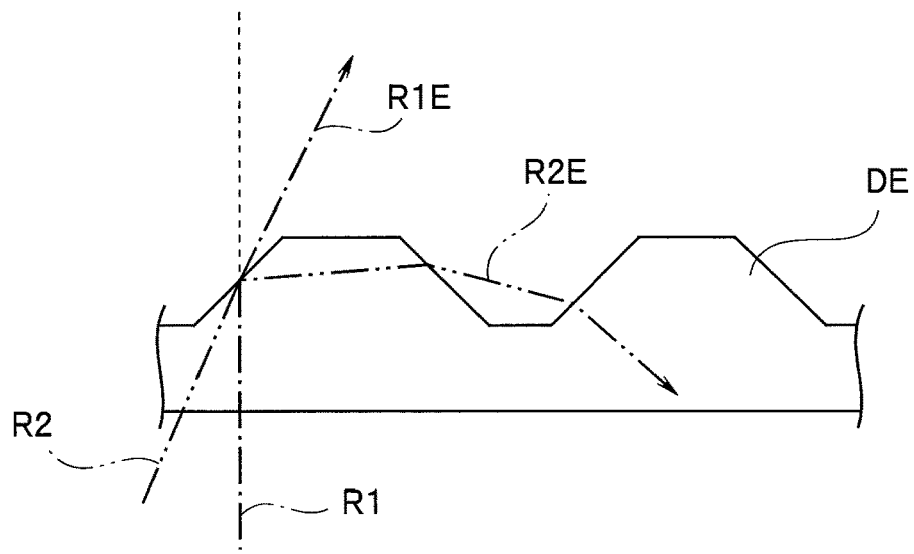
FIG. 27 is a diagram for explaining a decrease in a light amount in a diffusing element including an uneven surface, a sectional shape of the diffusing element being a trapezoidal shape.

Further, still another part of the light traveling toward the diffusing section DS is totally reflected on the slope section IP1 of the convex section P2 and refracted on the slope section IP2 to be light L3 to be emitted. Still another part of the light traveling toward the diffusing section DS is made incident on the slope section IP2 of the convex part P2 and refracted on the slope section IP2 to be light L4 to be emitted. As a result, the lights L1 and L2 and the lights L3 and L4 are emitted plane symmetrically with respect to the plane PP. Since each of the convex-shaped section UF includes the two convex sections P1 and P2, emitted light is emitted with little light distribution unevenness. When a diffusing element having an uneven surface, a sectional shape of which is a triangular shape, is simply used, return light occurs and a light amount decreases as shown in FIG. 27. However, by adopting a structure in which the diffusing section DS includes the steep slope IP1 and the gentle slope IP2 in this way, it is possible to emit light without causing return light and prevent a decrease in a light amount.

When depths of the groove G1 and the groove G2 are respectively represented as Ha and Hb and lengths in the axis O direction of the slope sections IP1 and IP2 when viewed in the direction OC are respectively represented as a and b as shown in FIG. 15, the depths Ha and Hb and the lengths a and b desirably have the following relation. Usually, incident light reaches the diffusing section DS at an angle of approximately 60°.

$$60° < \theta a \leq 85° \tag{1}$$

$$0° < \theta b \leq 30° \tag{2}$$

$$Ha \geq Hb \tag{3}$$

$$a \leq b \tag{4}$$

Expression (1) indicates a relation for totally reflecting the incident light on the slope section IP1. Expression (2) indicates a relation for transmitting, in the slope section IP2, reflected light from the slope section IP1. Expression (3) indicates a relation for transmitting more reflected light from the slope section IP1. Expression (4) indicates a relation for emitting from the slope section IP2 reflected light from the slope section IP1 with fewer loss. Expression (4) is also a relational expression for changing a light amount ratio of the lights L1 and L3 having a large angle at an emission time with respect to the plane PP and the lights L2 and L4 having a small angle at an emission time with respect to the plane PP and adjusting light distribution.

In other words, when viewed in the direction OC orthogonal to the axis O, an angle $\theta a$ is an angle in a range of an angle larger than 60° and equal to or smaller than 85° with respect to the emission surface 51a or 51b and an angle $\theta b$ is an angle in a range of an angle larger than 0° and equal to or smaller than 30° with respect to the emission surface 51a or 51b.

The depth Ha of the groove G1 formed by adjacent two slope sections IP1 (total reflection surfaces) is larger than the depth Hb of the groove G2 formed by adjacent two slope sections IP2 (transmission surfaces).

As explained above, each of the convex-shaped sections UF includes the slope sections IP1, which have the angle $\theta a$ with respect to the emission surface 51a or 51b and are the total reflection surfaces that totally reflect incident light, and the slope sections IP2. The slope sections IP2 are the transmission surfaces that have the angle $\theta b$ smaller than the angle $\theta a$ with respect to the emission surface 51a or 51b and transmit and emit reflected light totally reflected on the slope sections IP1 and incident light directly made incident on the slope sections IP2.

Each of the convex-shaped sections OF includes the two convex sections P1 and P2 respectively formed by total reflection surfaces and transmission surfaces to be plane symmetrical with respect to the plane (PP) orthogonal to the emission surface 51a or 51b and parallel to the predetermined direction.

According to a simulation performed by the applicant, in one-dimensional diffusing elements in which pluralities of diffusing sections DS, a sectional shape of which was an isosceles triangle, were disposed, respective slopes of the respective diffusing elements with respect to a bottom surface of the isosceles triangle being 10 degrees or 20 degrees, sufficient diffusion was not obtained in illumination light when light was made incident in a direction orthogonal to the bottom surface.

According to the simulation performed by the applicant, in one-dimensional diffusing elements in which pluralities of diffusing sections DS, a sectional shape of which was an isosceles triangle, were disposed, respective slopes of the respective diffusing elements with respect to a bottom surface of the isosceles triangle being 30 degrees, 40 degrees, 50 degrees, or 60 degrees, return light occurred in reflection on diffusion surfaces and a light amount decreased when light was made incident in a direction orthogonal to the bottom surface.

Further, according to the simulation performed by the applicant, in one-dimensional diffusing elements in which pluralities of diffusing sections DS, a sectional shape of which was an isosceles triangle, were disposed, respective slopes of the respective diffusing elements with respect to a bottom surface of the isosceles triangle being 70 degrees or 80 degrees, return light due to reflection on diffusion surfaces did not occur but light distribution unevenness occurred when light was made incident in a direction orthogonal to the bottom surface.

In contrast, according to the simulation in the embodiment explained above, when $\theta a$ was 75 degrees and $\theta b$ was 20 degrees, diffusion was obtained in the illumination light in the predetermined direction, return light due to reflection in the diffusing sections DS did not occur, and light distribution unevenness was little.

Figure 19:
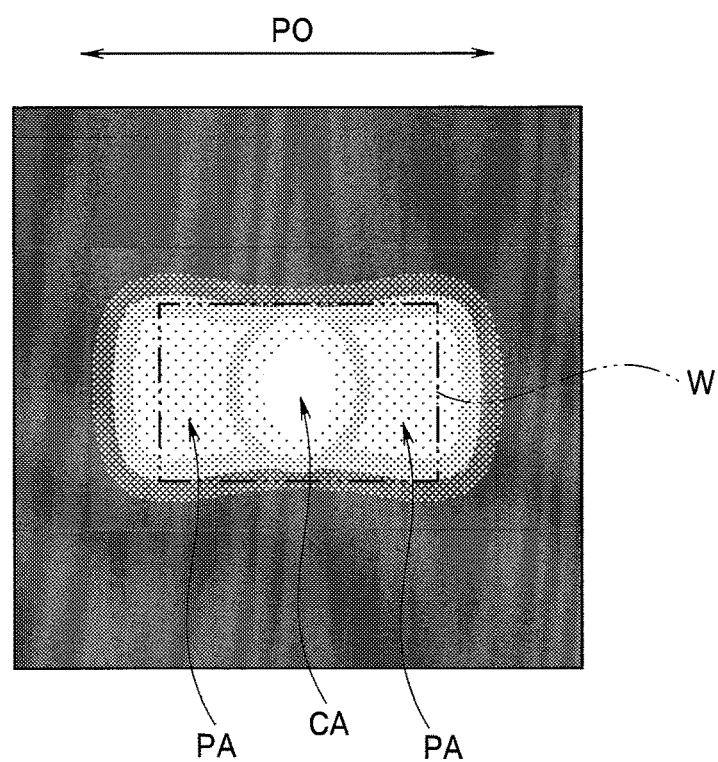
FIG. 19 is a diagram showing light distribution of illumination light at a time when an angle θa of the convex-shaped section is 75 degrees and an angle θb of the convex-shaped section is 20 degrees by a simulation performed by an applicant according to the first embodiment of the present invention.

FIG. 19 is a diagram showing light distribution of the illumination light at a time when the angle $\theta a$ of the convex-shaped section UF is 75 degrees and the angle $\theta b$ of the convex-shaped section UF is 20 degrees according to the simulation performed by the applicant. As shown in FIG. 19, a center region CA is illuminated most brightly but a peripheral region PA adjacent to the center region CA is also continuously illuminated brightly. Since a range of the illumination of the illumination light diffuses only in a predetermined direction PO, the range of the illumination of the illumination light diffuses in a predetermined one-dimensional direction (a lateral direction in FIG. 19) PO and light distribution unevenness is little. Accordingly, the illumination light can be emitted to be adjusted to, for example, an inside of a visual field frame W (indicated by an alternate long and two short dashes line) of an endoscopic image displayed on a monitor.

According to the simulation about the diffusing section DS in the embodiment explained above, when the angle $\theta a$ is 80 degrees and the angle $\theta b$ is 20 degrees as well, diffusion was obtained in the predetermined direction (the direction parallel to the axis O), return light due to reflection in the diffusing section DS did not occur, and light distribution unevenness was little.

Figure 20:
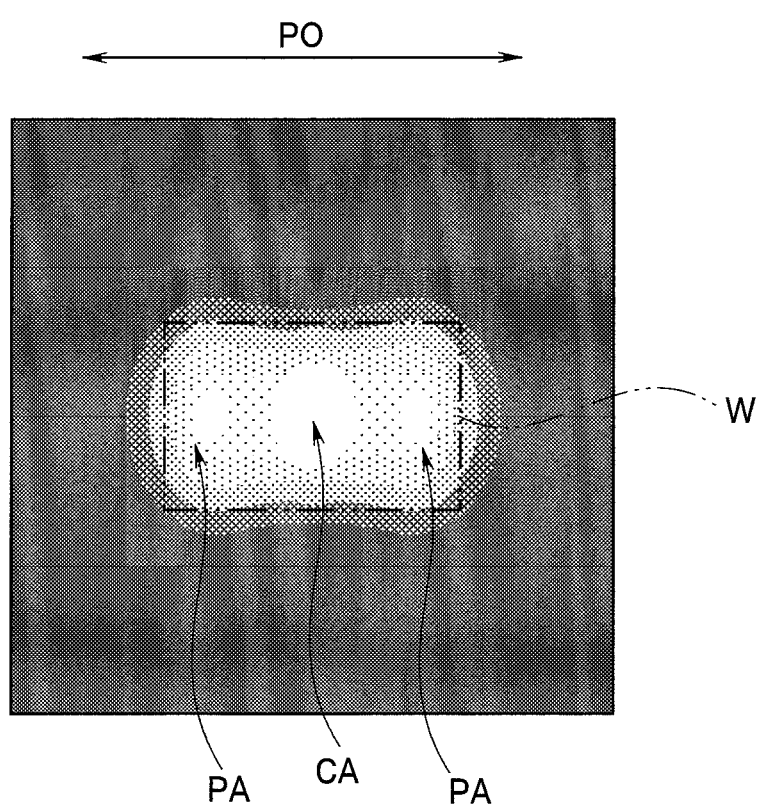
FIG. 20 is a diagram showing light distribution of illumination light at a time when the angle θa of the convex-shaped section is 80 degrees and the angle θb of the convex-shaped section is 20 degrees by the simulation performed by the applicant according to the first embodiment of the present invention.

FIG. 20 is a diagram showing light distribution of the illumination light at a time when the angle $\theta a$ of the convex-shaped section UF is 80 degrees and the angle $\theta b$ of the convex-shaped section UF is 20 degrees according to the simulation performed by the applicant. As shown in FIG. 20, the range of the illumination of the illumination light diffuses in the predetermined one-dimensional direction (the lateral direction in FIG. 20) PO and light distribution unevenness is little.

Therefore, according to Expressions (1) and (2) described above, there is no decrease in a light amount and diffusion of the illumination light in the predetermined direction can be performed. According to Expressions (3) and (4) described above, it is possible to reduce light distribution unevenness.

As explained above, according to the embodiment explained above, it is possible to provide an illumination optical system for endoscope and an optical adapter for endoscope that can diffuse illumination light only in a predetermined direction with little light distribution unevenness without reducing a light amount of the illumination light in a visual field.

Note that, in the embodiment explained above, the endoscope 3 is an endoscope for side view that emits illumination light in a direction orthogonal to the longitudinal axial direction of the insertion section 5 and observes an inside of a subject. However, the embodiment explained above is also applicable to an endoscope for perspective view that emits illumination light in an oblique direction with respect to the axis O of the insertion section 5 and observes an inside of a subject.

Modifications are explained below.

Modification 1

In the embodiment explained above, in order to reduce light distribution unevenness, each of the convex-shaped sections UF of the diffusing section DS includes the convex sections P1 and P2 plane symmetrical with respect to the plane PP. However, in the diffusing section DS, each of convex-shaped sections may include one convex section, a plurality of the convex-shaped sections may be disposed, and the plurality of convex-shaped sections may be disposed plane symmetrically.

Figure 21:
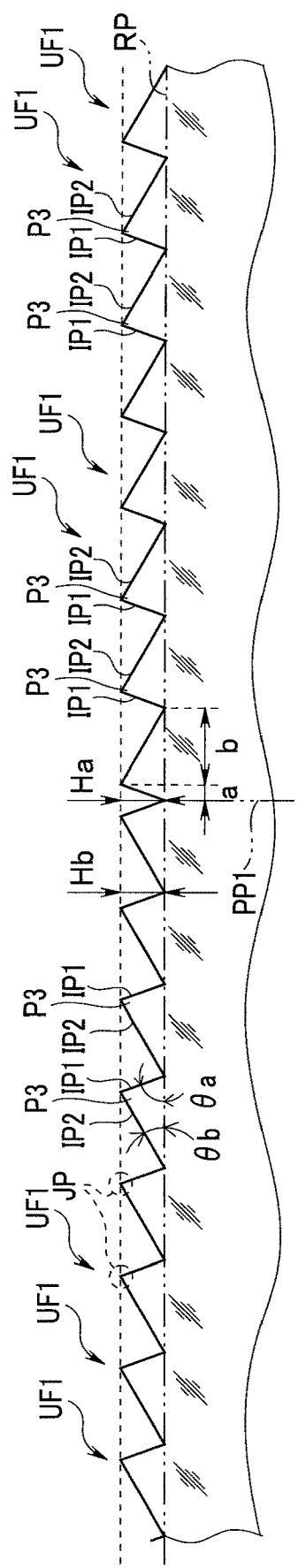
FIG. 21 is a sectional view showing a shape of a cross section of a diffusing section including a plurality of convex-shaped sections according to a modification 1 of the first embodiment of the present invention.

FIG. 21 is a sectional view showing a shape of a cross section of a diffusing section including a plurality of convex-shaped sections UF1 according to a modification 1. FIG. 21 shows a cross section of a part of the diffusing section DS at a time when the emission surface 51a or 51b is viewed in the direction OC.

In the modification 1, each of the convex-shaped sections UF1 includes the slope sections IP1 and IP2. The plurality of convex-shaped sections UF1 are formed to linearly extend in the direction OC orthogonal to the axis O on the emission surface 51a or 51b. Each of the convex-shaped sections UF1 includes one convex section P3. As shown in FIG. 21, the convex section P3 is formed by one slope section IP1 and one slope section IP2.

Further, halves of the plurality of convex-shaped sections UF1 are disposed to be plane symmetrical to each other with respect to a plane PP1 orthogonal to the axis O. The halves of the plurality of convex-shaped sections UFI are disposed to be plane symmetrical to each other on the emission surface 51a or 51b with respect to the plane PPT shown in FIG. 21.

In other words, a part of the plurality of convex-shaped sections UF1 is disposed on the emission surface 51a or 51b plane symmetrically to another part of the plurality of convex-shaped sections UF1 with respect to the plane PP1 parallel to the direction OC orthogonal to the axis O.

In the modification 1, Expression (1), Expression (2), and Expression (4) described above hold. However, a relation of Equation (5) described below holds instead of Expression (3) described above.

$$Ha=Hb \quad (5)$$

According to the modification 1 as well, the same effects as the effects in the embodiment explained above can be obtained.

Modification 2

In the modification 1 explained above, in order to reduce light distribution unevenness, the diffusing section DS includes the plurality of convex-shaped sections UF1 plane symmetrical with respect to one plane PP1. However, the diffusing section DS may include a plurality of convex-shaped section groups including plane-symmetrically disposed pluralities of convex-shaped sections, each of which includes one convex section.

Figure 22:
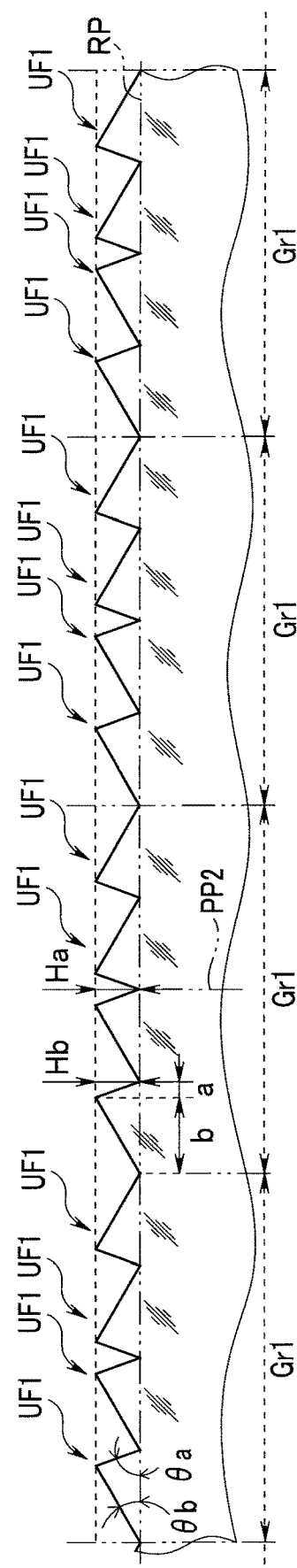
FIG. 22 is a sectional view showing a shape of a cross section of a diffusing section including a plurality of convex-shaped sections according to a modification 2 of the first embodiment of the present invention.

FIG. 22 is a sectional view showing a shape of a cross section of a diffusing section including a plurality of convex-shaped sections UF1 according to a modification 2. FIG. 22 shows a cross section of a part of the diffusing section DS at a time when the emission surface 51a or 51b is viewed in the direction OC. Each of the convex-shaped sections UF1 in the modification 2 has the same shape as the shape of the convex-shaped section UF1 in the modification 1.

As shown in FIG. 22, a plurality of (two) convex-shaped sections UF1 are disposed to be plane symmetrical to one another with respect to a plane PP2 orthogonal to the axis O. The diffusing section DS is formed such that a plurality of convex-shaped section groups Gr1 including plane symmetrical pluralities of (four) convex-shaped sections UF1 are disposed on the emission surface 51a or 51b. In other words, the diffusing section DS includes a plurality of regions of the convex-shaped section groups Gr1.

In other words, a plurality of regions are provided where a part of the plurality of convex-shaped sections UF1 and another part of the plurality of convex-shaped sections UF1 are disposed on the emission surface 51a or 51b plane symmetrically with respect to the plane PP2 parallel to the direction OC.

In the modification 2 as well, Expression (1), Expression (2), and Expression (4) described above hold. However, the relation of Equation (5) described above holds instead of Expression (3) described above.

According to the modification 2 as well, the same effects as the effects in the embodiment explained above can be obtained.

Modification 3

In the example explained above, the convex-shaped section has portions plane symmetrical to each other on the emission surface with respect to a predetermined plane. However, for example, the convex-shaped section may not include plane symmetrical portions in a range in which light distribution to left and right is not markedly affected.

More specifically, the angles of the slope sections IP2, which are the gentle slopes, may be respectively changed and the lengths b of the slope sections IP2 may be respectively set to a different value in each of the convex-shaped sections. Consequently, even if the disposition of the convex-shaped sections is not plane symmetrical, nonuniformity of light distribution unevenness on left and right can be reduced if appropriate design is performed in an element as a whole. Note that not only the angles and the lengths of the gentle slopes but also the angles and the lengths a of the slope sections IP1, which are the steep slopes, may be changed as appropriate.

According to the modification 3 as well, return light decreases and a light amount can be increased.

Modification 4

In the modifications 1 and 2 explained above, the plurality of convex-shaped sections have the plane symmetrically disposed portions. However, the plurality of convex-shaped sections may not be plane symmetrically disposed.

In the modification 4, the plurality of convex-shaped sections UF1 are not disposed to be plane symmetrical to one another on the emission surface 51a or 51b with respect to the plane PP1 as shown in FIG. 21 in the modification 1 explained above. Accordingly, in the case of the modification 4, a light distribution direction deviates to one direction.

Figure 23:
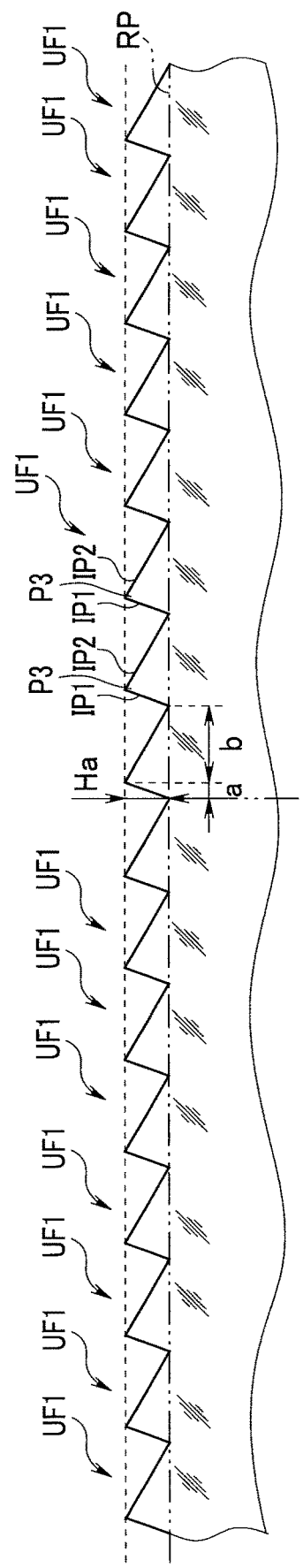
FIG. 23 is a sectional view showing a shape of a cross section of a diffusing section including a plurality of convex-shaped sections according to a modification 4 of the first embodiment of the present invention.

FIG. 23 is a sectional view showing a shape of a cross section of a diffusing section including a plurality of convex-shaped sections UF1 according to the modification 4. FIG. 23 shows a cross section of a part of the diffusing section DS at a time when the emission surface 51a or 51b is viewed in the direction OC. Each of the convex-shaped sections UF1 in the modification 4 has the same shape as a shape of one side portion (a left side portion in FIG. 21) of the plane symmetrical plurality of convex-shaped sections UF1 in the modification 1.

As shown in FIG. 23, the diffusing section DS is formed such that the plurality of convex-shaped sections UF1 having the same sectional shape are disposed on the emission surface 51a or 51b. In other words, the slope sections IP1 and IP2 of each of the convex-shaped sections UF1 respectively have the same angles as angles of the slope sections IP1 and IP2 of the other convex-shaped sections UF1 with respect to the imaginary plane RP parallel to the direction OC.

In the modification 4 as well, Expression (1), Expression (2), and Expression (4) described above hold. However, the relation of Equation (5) described above holds instead of Expression (3) described above.

Therefore, the modification 4 is effective when it is desired to, for example, deviate light distribution in one direction.

According to the modification 4 as well, return light decreases and a light amount can be increased.

Note that, in the modifications 1 to 4 as well, the bonded section JP of the slope sections IP1 and IP2 in each of the convex sections P1 and P2 may not be sharp and, for example, may have a round shape or may have a chamfered shape cut on multiple surfaces.

Second Embodiment

The endoscope apparatus in the first embodiment is the endoscope apparatus for side view. However, an endoscope of an endoscope apparatus in a second embodiment is an endoscope for front view that emits illumination light to a front of the distal end portion 11 from the illumination window of the distal end portion 11 in the longitudinal axial direction of the insertion section 5.

A configuration of the endoscope apparatus in the present embodiment is substantially the same as the configuration of the endoscope apparatus in the first embodiment. Therefore, in the configuration of the endoscope apparatus in the present embodiment, the same components as the components of the endoscope apparatus in the first embodiment are denoted by the same reference numerals and signs. Explanation of the components is omitted. Only different components are explained.

Figure 24:
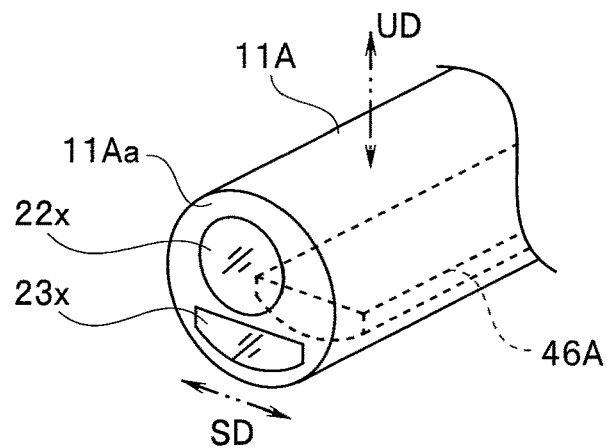
FIG. 24 is a perspective view of a distal end portion of an endoscope according to a second embodiment of the present invention.

FIG. 24 is a perspective view of a distal end portion 11A of the endoscope 3. An observation window 22x and an illumination window 23x are provided on a distal end face 11Aa of the distal end portion 11A. Illumination light is emitted from the illumination window 23x. Reflected light of the illumination light reflected by an object is made incident on the observation window 22x. The reflected light made incident on the observation window 22x is irradiated on an image pickup surface of the image pickup device 11x through a not-shown observation optical system.

The illumination window 23x has a shape extending in a lateral direction SD according to a shape of a rectangular endoscopic image displayed on a monitor.

A light guide (not shown) for guiding the illumination light is inserted through the insertion section 5. A rod lens 46A having a partial columnar shape is provided on a distal end side of the light guide.

Figure 25:
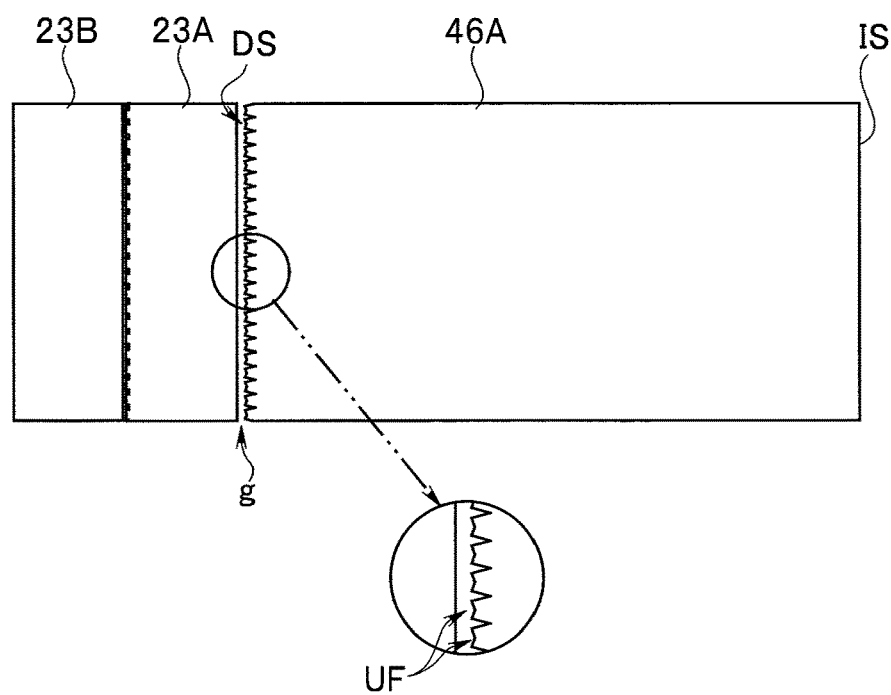
FIG. 25 is a plan view showing disposition of two optical elements and a rod lens in the distal end portion according to the second embodiment of the present invention.

FIG. 25 is a plan view showing disposition of two optical members 23A and 23B and the rod lens 46A in the distal end portion 11A. FIG. 25 shows disposition of the two optical members 23A and 23B and the rod lens 46A at a time when the distal end portion 11A is viewed from an upper side in an up-down direction UD orthogonal to the lateral direction SD. An incident surface IS of the rod lens 46A and an emission surface on which the diffusing section DS is formed are parallel.

For example, the rod lens 46A is made of plastic and has a refractive index of 1.5. The optical members 23A and 23B are disposed via the gap g of the air having a refractive index of 1. The optical members 23A are respectively bonded and fixed to the optical members 23B by an optical adhesive (not shown). A sand grain surface (indicated by a dotted line) side of the optical members 23A is bonded to the optical members 23B by the optical adhesive not shown). The optical members 23A and 23B are made of glass and have a refractive index of 1.8. More specifically, a refractive index of the optical adhesive only has to be a value such as 1.52 or 1.56, that is, a value smaller than a refractive index of the optical members 23A and 23B and larger than 1, which is the refractive index of the air.

The diffusing section DS including a plurality of convex-shaped sections UF is provided on a distal end face of the rod lens 46A. A shape of the convex-shaped section UF of the diffusing section DS is the same as the shape of the convex-shaped section UF in the first embodiment but may be the shape explained above in the modification 1 or the modification 2.

In other words, the diffusing section DS includes the plurality of convex-shaped sections UF linearly extending in a predetermined direction on an emission surface of the rod lens 46A. The diffusing section DS can be formed by molding when the rod lens 46A is manufactured. Therefore, workability is high.

Two optical members 23A and 23B made of glass are disposed on a distal end face side of the rod lens 46A via the gap g of the air. The optical members 23A and 23B are bonded and fixed by a not-shown optical adhesive. A sand grain surface (indicated by a dotted line) machined into a frosted glass form is provided on a surface of the optical member 23A on the optical member 23B side.

Therefore, according to the embodiment explained above as well, it is possible to provide an illumination optical system for endoscope and an optical adapter for endoscope that can diffuse illumination light only in a predetermined direction with little light distribution unevenness without reducing a light amount of the illumination light in a visual field.

Note that it is also conceivable to provide the diffusing section DS on the incident surface IS side of the rod lens 46A. However, in the case, there is a problem that when light is emitted from the emission surface passing through the rod lens 46A, the light entering the rod lens 46A leaks from a side surface of the rod lens 46A and a light amount of emitted light from the emission surface decreases.

Furthermore, in FIGS. 24 and 25, the rod lens 46A functioning as the optical element is disposed in the distal end portion 11A of the insertion section 5. However, the rod lens 46A may be disposed in the optical adapter 10 attachable to the distal end portion 11 of the insertion section 5 shown in FIG. 1.

Modification

In the second embodiment explained above, the rod lens 46A provided on the distal end side of the light guide includes the diffusing section DS. However, an optical element may be disposed between an incident surface on the proximal end side of the rod lens and the distal end face of the light guide. The optical element may include the diffusing section DS.

Figure 26:
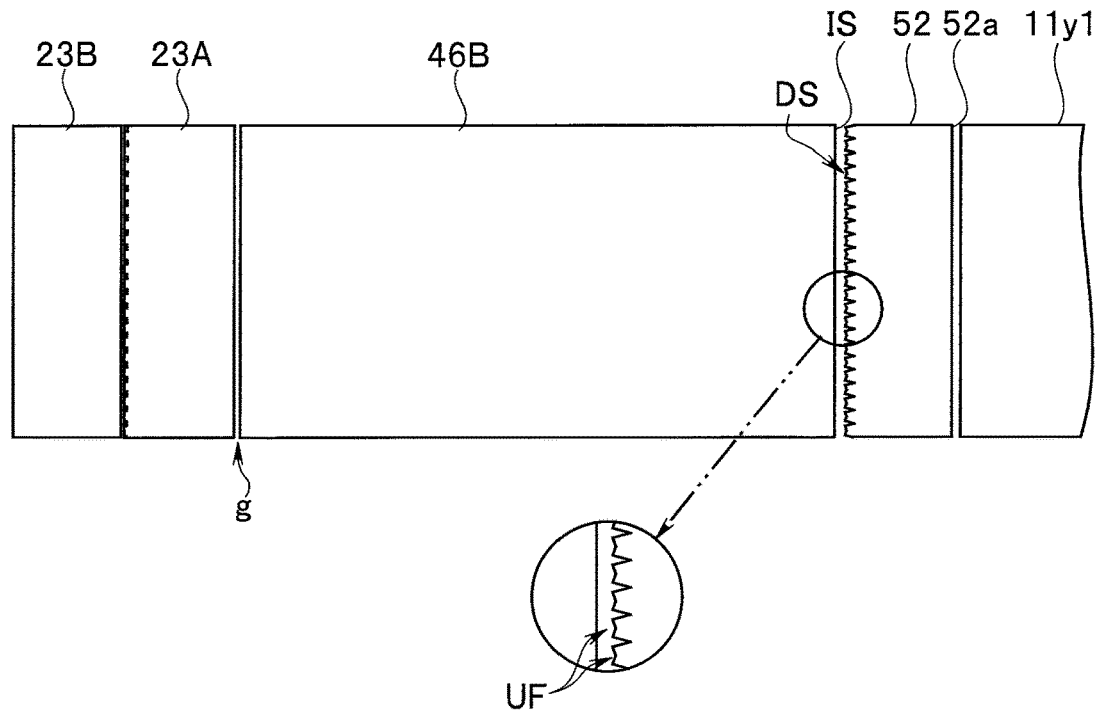
FIG. 26 is a plan view showing disposition of two optical elements and a rod lens in a distal end portion according to a modification 4 of the second embodiment of the present invention.

FIG. 26 is a plan view showing disposition of two optical elements and a rod lens in a distal end portion according to a modification of the second embodiment. FIG. 26 shows disposition of the two optical members 23A and 23B, a rod lens 46B, an optical element 52, and a light guide 11y1 at a time when the distal end portion 11A is viewed from an upper side in the up-down direction UD orthogonal to the lateral direction SD. The incident surface IS of the rod lens 46B and an emission surface (a portion where the diffusing section DS is formed) of the optical element 52 are parallel. An incident surface 52a of the optical element 52 and a distal end face of the light guide 11y1 are also parallel.

As shown in FIG. 26, the optical element 52 is disposed between the distal end face of the light guide 11y1 and a proximal end face of the rod lens 46B. The optical element 52 is glass (or plastic) having a flat shape. The incident surface 52a of the optical element 52 includes a plane. The emission surface of the optical element 52 includes the diffusing section DS. The diffusing section DS includes a plurality of convex-shaped sections UF linearly extending in a predetermined direction on the emission surface of the optical element 52. As shown in FIG. 26, the convex-shaped section UF has the same shape as the shape of the convex-shaped section UF of the diffusing section DS of the rod lens 46A shown in FIG. 25 explained above.

Light made incident on the incident surface 52a of the optical element 52 is diffused in the diffusing section DS, which is an emitting section of the optical element 52 and emitted. The diffused light reflects and travels in various directions on an inside of the rod lens 46B and emitted from an emission surface OS of the rod lens 46B to spread.

The light emitted from the optical element 52 is diffused by the diffusing section DS to have spread in the lateral direction SD (the up-down direction in FIG. 26). However, since the rod lens 46B has a partially columnar shape, the light from the diffusing section DS is also reflected in various directions other than the lateral direction SD on the inside of the rod lens 46B.

As a result, the light emitted from the emission surface of the rod lens 46B is diffused and emitted not only in the lateral direction SD but also in various directions. Therefore, it is possible to obtain the same effects as the effects in the second embodiment explained above.

Third Embodiment

The first and second embodiments relate to the substantially U-shaped light transmission optical member 51 or the rod lens 46A functioning as the optical element used in the endoscope. However, the optical element including the diffusing section DS explained in the first and second embodiments can also be used in an apparatus other than the endoscope apparatus as an optical element that diffuses illumination light only in a predetermined direction with little light distribution unevenness without reducing a light amount of the illumination light in a visual field.

Note that, in the second and third embodiments, the bonded section JP of the slope sections IP1 and IP2 in each of the convex sections P1, P2, and P3 may not be sharp and, for example, may have a round shape or may have a chamfered shape cut on multiple surfaces.

As explained above, according to the respective embodiments explained above, it is possible to provide an illumination optical system for endoscope, an optical adapter for endoscope, and an optical element that can diffuse illumination light only in a predetermined direction with little light distribution unevenness without reducing a light amount of the illumination light in a visual field.

The present invention is not limited to the embodiments explained above. Various changes, alterations, and the like are possible in a range in which the gist of the present invention is not changed.

What is claimed is:

1. An illumination optical system configured for use with an endoscope, the illumination optical system comprising:
    an optical element comprising:
        an incident surface configured to connect to a distal end portion of an insertion section of the endoscope, light from the distal end of the insertion section being made incident on the incident surface as incident light, and
        an emission surface for emitting the light as illumination light,
    wherein the emission surface includes a diffusing section that diffuses the emitted light,
    the diffusing section includes a plurality of convex-shaped sections extending in a predetermined direction on the emission surface, and
    each of the convex-shaped sections comprising:
        a total reflection surface having a first angle with respect to the emission surface, the total reflection surface totally reflecting the incident light, and
        a transmission surface having a second angle smaller than the first angle with respect to the emission surface, the transmission surface transmitting and emitting reflected light totally reflected on the total reflection surface and the incident light.

2. The illumination optical system according to claim 1, wherein each of the convex-shaped sections includes two convex sections, each of which is formed by the total reflection surface and the transmission surface to be plane symmetrical with respect to a surface orthogonal to the emission surface and parallel to the predetermined direction.

3. The illumination optical system according to claim 1, wherein when viewed in the predetermined direction, the first angle is equal to or larger than 60° and equal to or smaller than 85° with respect to the emission surface and the second angle is larger than 0° and equal to or smaller than 30° with respect to the emission surface.

4. The illumination optical system according to claim 2, wherein a depth of a first groove formed by two adjacent total reflection surfaces is larger than a depth of a second groove formed by two adjacent transmission surfaces.

5. The illumination optical system according to claim 1, wherein a part of the plurality of convex-shaped sections is disposed in a same plane as another part of the plurality of convex-shaped sections, and the plane has a dimension that extends in a same direction as the predetermined direction.

6. The illumination optical system according to claim 1, wherein a plurality of regions are provided where a part of the plurality of convex-shaped sections is disposed on a same plane as another part of the plurality of convex-shaped sections, and the plane has a dimension that extends in a same direction as the predetermined direction.

7. The illumination optical system according to claim 1, wherein the illumination optical system for endoscope is an illumination optical system for an endoscope for front view, perspective view, or side view.

8. The illumination optical system according to claim 7, wherein when the illumination optical system is for a front view, the optical element is a rod lens.

9. The illumination optical system according to claim 7, wherein when the illumination optical system is for a side view, the optical element is a prism having one of a substantial U shape or a shape of a part of the substantial U shape, the prism including two reflection surfaces for reflecting the incident light.

10. The illumination optical system according to claim 1, further comprising:
   a first optical member provided on a side of the emission surface of the optical element and including a sand grain surface on an opposite side of the side of the emission surface; and
   a second optical member bonded to the first optical member by an adhesive on the sand grain surface.

11. An optical adapter configured for use with an endoscope, the optical adapter comprising:
   an optical element comprising:
      an incident surface configured to connect to a distal end portion of an insertion section of the endoscope, light from the distal end of the insertion section being made incident on the incident surface as incident light, and
      an emission surface for emitting the light as illumination light; and
   an illumination window for emitting the illumination light emitted from the emission surface of the optical element,
   wherein the emission surface includes a diffusing section that diffuses the emitted light,
   the diffusing section includes a plurality of convex-shaped sections extending in a predetermined direction on the emission surface, and
   each of the convex-shaped sections comprising:
      a total reflection surface having a first angle with respect to the emission surface, the total reflection surface totally reflecting the incident light, and
      a transmission surface having a second angle smaller than the first angle with respect to the emission surface, the transmission surface transmitting and emitting reflected light totally reflected on the total reflection surface and the incident light.

12. The optical adapter according to claim 11, wherein the optical adapter for endoscope emits the illumination light from the illumination window in a direction orthogonal to a longitudinal axial direction of the optical adapter or at an angle intersecting the longitudinal axial direction.

13. The optical adapter according to claim 11, wherein the optical adapter for endoscope emits the illumination light from the illumination window to a front of the distal end portion in a longitudinal axial direction of the optical adapter.

14. An optical element comprising:
   an incident surface on which light is made incident as incident light; and
   an emission surface for emitting the light as emitted light,
   wherein the emission surface includes a diffusing section that diffuses the emitted light,
   the diffusing section includes a plurality of convex-shaped sections extending in a predetermined direction on the emission surface, and
   each of the convex-shaped sections comprising:
      a total reflection surface having a first angle with respect to the emission surface, the total reflection surface totally reflecting the incident light, and
      a transmission surface having a second angle smaller than the first angle with respect to the emission surface, the transmission surface transmitting and emitting reflected light totally reflected on the total reflection surface and the incident light.

* * * * *